US011246856B2

(12) United States Patent
Eckert et al.

(10) Patent No.: US 11,246,856 B2
(45) Date of Patent: Feb. 15, 2022

(54) METHODS OF TREATING RESISTANT CANCERS

(71) Applicant: University of Maryland, Baltimore, Baltimore, MD (US)

(72) Inventors: Richard L. Eckert, Baltimore, MD (US); Matthew Fisher, Smithtown, NY (US); Daniel Grun, Derwood, MD (US); Gautam Adhikary, Ellicott City, MD (US); Wen Xu, Ellicott City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 16/614,147

(22) PCT Filed: May 18, 2018

(86) PCT No.: PCT/US2018/033457
§ 371 (c)(1),
(2) Date: Nov. 15, 2019

(87) PCT Pub. No.: WO2018/213748
PCT Pub. Date: Nov. 22, 2018

(65) Prior Publication Data
US 2020/0147047 A1 May 14, 2020

Related U.S. Application Data

(60) Provisional application No. 62/507,837, filed on May 18, 2017.

(51) Int. Cl.
| | | |
|---|---|---|
| *A61K 31/409* | (2006.01) |
| *A61P 35/00* | (2006.01) |
| *A61K 31/437* | (2006.01) |
| *A61K 31/44* | (2006.01) |
| *A61K 31/506* | (2006.01) |
| *A61K 45/06* | (2006.01) |

(52) U.S. Cl.
CPC .......... *A61K 31/409* (2013.01); *A61K 31/437* (2013.01); *A61K 31/44* (2013.01); *A61K 31/506* (2013.01); *A61K 45/06* (2013.01); *A61P 35/00* (2018.01)

(58) Field of Classification Search
CPC .............................. A61K 31/409; A61P 35/00
See application file for complete search history.

(56) References Cited

U.S. PATENT DOCUMENTS

2004/0110731 A1* 6/2004 Chan .................. A61K 41/0071
514/169
2017/0112865 A1  4/2017 Morrison et al.

FOREIGN PATENT DOCUMENTS

WO   2017035116 A1   2/2017

OTHER PUBLICATIONS

Wachtlin et al. Ophthalmologe, 2005, 102(3): 241-246.*
Kelleher et al., Journal of Personalized Medicine, 2012, 2(2):35-49.*
Davies et al. Mutations of the BRAF gene in human cancer. Nature 2002; 417: 949-954.
Lito et al. Relief of profound feedback inhibition of mitogenic signaling by RAF inhibitors attenuates their activity in BRAFV600E melanomas. Cancer Cell 2012; 22: 668-682.
Spagnolo et al. Overcoming resistance to BRAF inhibition in BRAF-mutated metastatic melanoma. Oncotarget 2014; 5: 10206-10221.
Hauschild et al. Dabrafenib in BRAF-mutated metastatic melanoma: a multicentre, open-label, phase 3 randomised controlled trial. Lancet 2012; 380: 358-365.
McArthur et al. Safety and efficacy of vemurafenib in BRAFV600E and BRAFV600K mutation-positive melanoma (BRIM-3): extended follow-up of a phase 3, randomised, open-label study Lancet Oncol 2014; 15: 323-332.
Johnson R, Halder G. The two faces of Hippo: targeting the Hippo pathway for regenerative medicine and cancer treatment Nat Rev Drug Discov 2014; 13: 63-79.
Harvey et al., The Hippo pathway and human cancer. Nat Rev Cancer 2013; 13: 246-257.
Lamar et al.. The Hippo pathway target, YAP, promotes metastasis through its TEAD-interaction domain. Proc Natl Acad Sci U S A 2012; 109: E2441-E2450.
Yuan et al., Genetic variants in Hippo pathway genes YAP1, TEAD1 and TEAD4 are associated with melanoma-specific survival. Int J Cancer 2015; 137: 638-645.
Menzel et al. In melanoma, Hippo signaling is affected by copy number alterations and YAP1 overexpression impairs patient survival. Pigment Cell Melanoma Res 2014; 27: 671-673.
Nallet-Staub et al.. Pro-invasive activity of the Hippo pathway effectors YAP and TAZ in cutaneous melanoma. J Invest Dermatol 2014; 134:123-132.
Lin et al. The Hippo effector YAP promotes resistance to RAF- and MEK-targeted cancer therapies. Nat Genet 2015; 47: 250-256.
Kim et al., Actin remodeling confers BRAF inhibitor resistance to melanoma cells through YAP/TAZ activation. EMBO J 2016; 35: 462-478.

(Continued)

*Primary Examiner* — Rei Tsang Shiao
(74) *Attorney, Agent, or Firm* — Benjamin Aaron Adler

(57) ABSTRACT

Provided herein is a method for reducing resistance in an individual having a drug resistant cancer, for example, a BRAF inhibitor resistant cancer. A Hippo signaling pathway inhibitor such as a Yes-associated protein 1 (YAP1) inhibitor, a Transcriptional Coactivator with PDZ-binding motif (TAZ) inhibitor, a Transcription enhancer domain (TEAD) inhibitor or a combination of these is administered. Also provided is a method of treating BRAF inhibitor resistance in an individual with a BRAF inhibitor resistant cancer, for example, malignant melanoma, with a Hippo signaling pathway inhibitor, such as Verteporfin, and a BRAF inhibitor.

8 Claims, 28 Drawing Sheets

Specification includes a Sequence Listing.

(56) References Cited

OTHER PUBLICATIONS

Zanconato F, Piccolo S. Eradicating tumor drug resistance at its YAP-biomechanical roots. EMBO J 2016; 35: 459-461.
Michels S, Schmidt-Erfurth U. Photodynamic therapy with verteporfin: a new treatment in ophthalmology. Semin Ophthalmol 2001; 16:201-206.
Liu-Chittenden et al., Genetic and pharmacological disruption of the TEAD-YAP complex suppresses the oncogenic activity of YAP. Genes Dev 2012; 26: 1300-1305.
Donohue et al., The autophagy inhibitor verteporfin moderately enhances the antitumor activity of gemcitabine in a pancreatic ductal adenocarcinoma model. J Cancer 2013; 4: 585-596.
Slemmons et al., Role of the YAP Oncoprotein in Priming Ras-Driven Rhabdomyosarcoma. PLoS One 2015; 10: e0140781.
Wagle et al., Dissecting therapeutic resistance to RAF inhibition in melanoma by tumor genomic profiling. J Clin Oncol 2011; 29: 3085-3096.
Song et al. The Hippo Coactivator YAP1 Mediates EGFR Overexpression and Confers Chemoresistance in Esophageal Cancer. Clin Cancer Res 2015; 21: 2580-2590.
Errico A. Targeted therapies: Hippo effector YAP1 inhibition—towards a new therapeutic option to overcome drug resistance. Nat Rev Clin Oncol 2015; 12: 190.
Greten Fr. YAP1 takes over when oncogenic K-Ras slumbers. Cell 2014; 158: 11-12.
Jerhammar et al., YAP1 is a potential biomarker for cetuximab resistance in head and neck cancer. Oral Oncol 2014; 50: 832-839.
Lee et al., Significant association of oncogene YAP1 with poor prognosis and cetuximab resistance in colorectal cancer patients. Clin Cancer Res 2015; 21: 357-364.
Liao et al., Yes-associated protein 1 promotes papillary thyroid cancer cell proliferation by activating the ERK/MAPK signaling pathway. Oncotarget2017; 8: 11719-11728.
Fisher et al., The Ezh2 polycomb group protein drives an aggressive phenotype in melanoma cancer stem cells and is a target of diet derived sulforaphane. Mol Carcinog 2015; 55: 2024-2036.

Fisher et al., Transglutaminase Interaction with $\alpha 6/\beta 4$-Integrin Stimulates YAP1-Dependent $\Delta Np63\alpha$ Stabilization and Leads to Enhanced Cancer Stem Cell Survival and Tumor Formation. Cancer Res 2016; 76: 7265-7276.
Halder G and Johnson RL. Hippo signaling: growth control and beyond. Development 2011; 138: 9-22.
Huang et al., The N-terminal phosphodegron targets TAZ/WWTR1 protein for SCF$\beta$-TrCP-dependent degradation in response to phosphatidylinositol 3-kinase inhibition. J Biol Chem 2012; 287: 26245-26253.
Gulshan et al., Proteolytic degradation of the Yap1 transcription factor is regulated by subcellular localization and the E3 ubiquitin ligase Not4. J Biol Chem 2012; 287: 26796-26805.
Wong et al., Antitumor activity of the ERK inhibitor SCH772984 [corrected] against BRAF mutant, NRAS mutant and wild-type melanoma. Mol Cancer 2014; 13: 194.
Joseph et al., The RAF inhibitor PLX4032 inhibits ERK signaling and tumor cell proliferation in a V600E BRAF-selective manner. Proc Natl Acad Sci U S A 2010; 107: 14903-14908.
Lin L. and Bivona TG, The Hippo effector YAP regulates the response of cancer cells to MAPK pathway inhibitors. Mol Cell Oncol 2016; 3: e1021441.
Moroishi et al., The emerging roles of YAP and TAZ in cancer. Nat Rev Cancer 2015; 15: 73-79.
Santucci et al., The Hippo Pathway and YAP/TAZ-TEAD Protein-Protein Interaction as Targets for Regenerative Medicine and Cancer Treatment. J Med Chem 2015; 58: 4857-4873.
Zhang et al., Biochemistry 2015.
Zhao et al., The Hippo-YAP pathway: new connections between regulation of organ size and cancer. Curr Opin Cell Biol 2008; 20: 638-646.
Adhikary et al., Survival of skin cancer stem cells requires the Ezh2 polycomb group protein. Carcinogenesis 2015; 36: 800-810.
Nakatani et al., Targeting the Hippo signalling pathway for cancer treatment. The Journal of Biochemistry 2017; 161, 237-244.
Morris V et al., F1000Prime Rep. 2013; 5, 1-6.

* cited by examiner

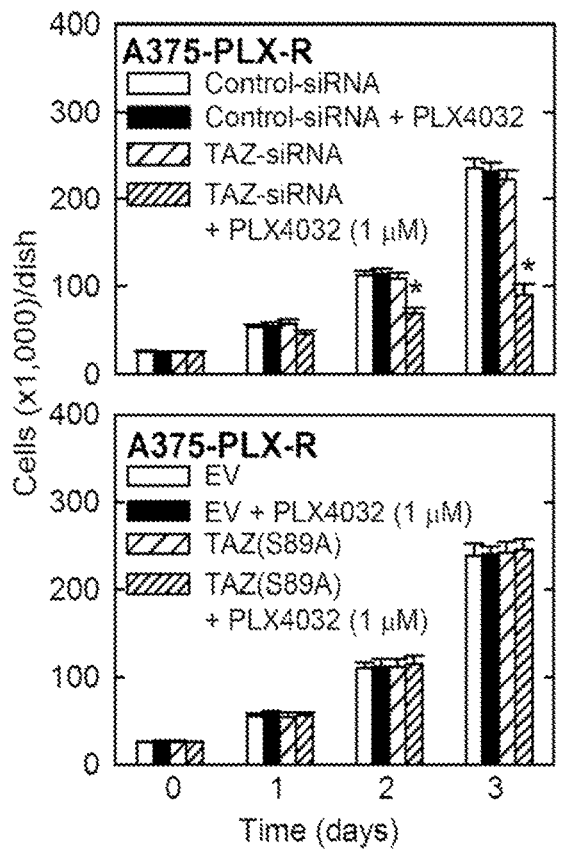
FIG. 1G
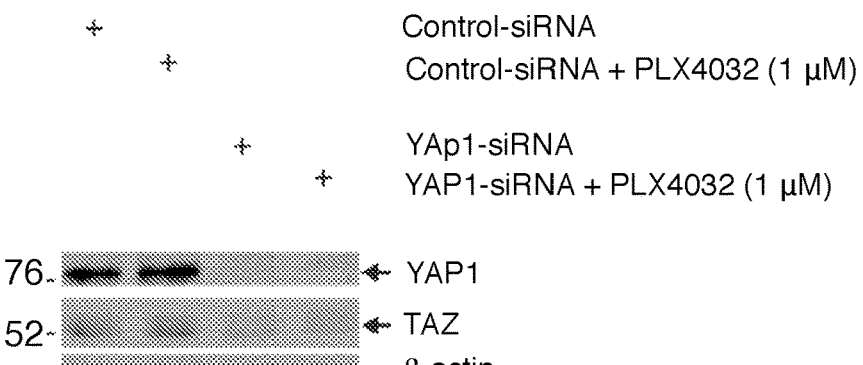
FIG. 1H
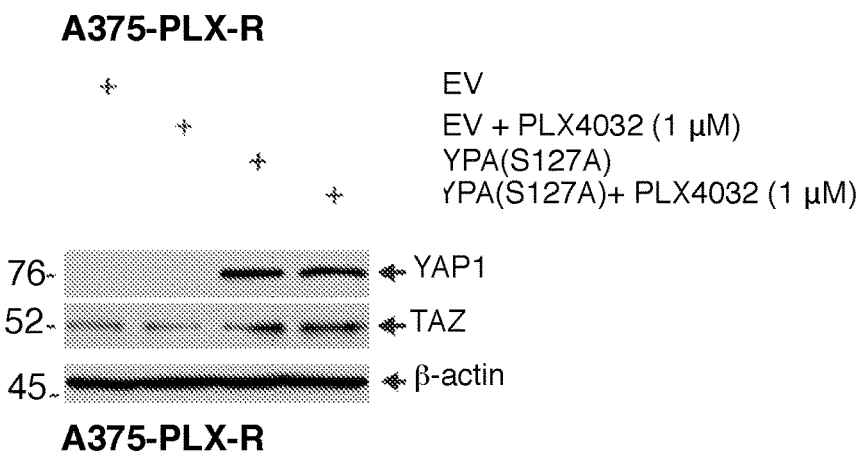

A375-PLX-R

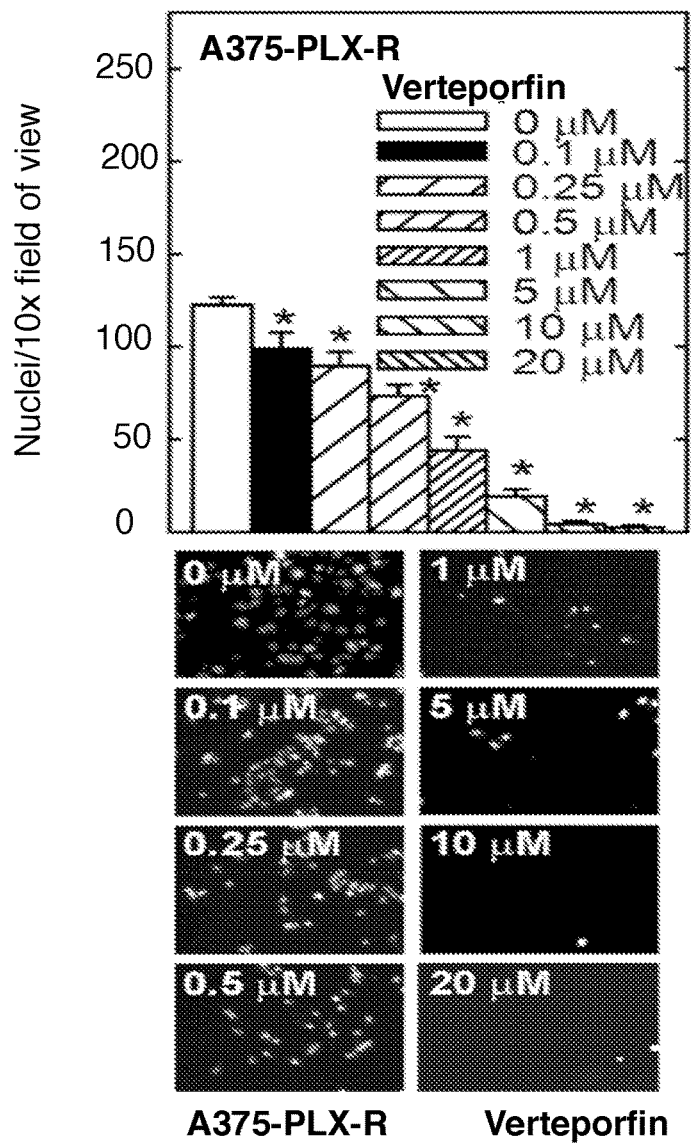
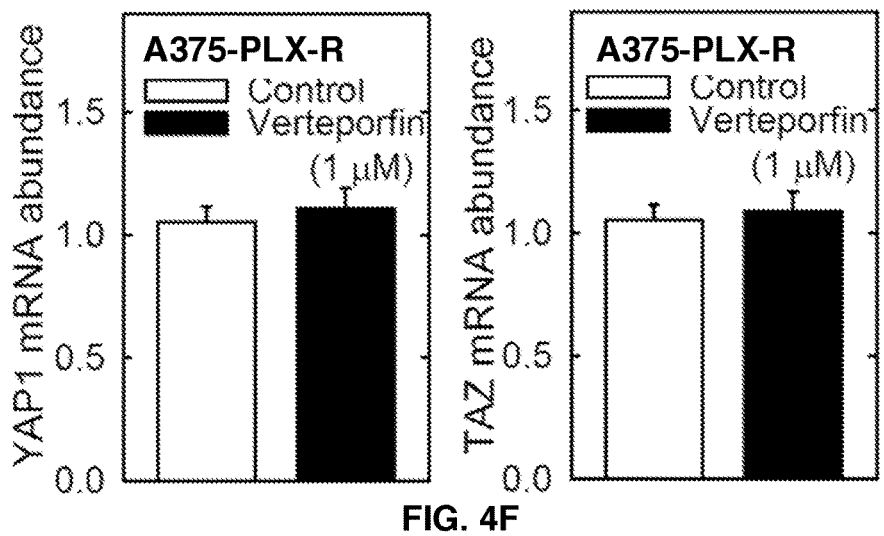
FIG. 4E
FIG. 4F

SEQUENCE LISTING

```
<160> NUMBER OF SEQ ID NOS: 8

<210> SEQ ID NO 1
<211> LENGTH: 12
<212> TYPE: PRT
<213> ORGANISM: Artificial Sequence
<220> FEATURE:
<223> OTHER INFORMATION: Sequence of the Hippo signaling pathway
      inhibitor BI-107F7
<220> FEATURE:
<221> NAME/KEY: MOD_RES
<222> LOCATION: 1
<223> OTHER INFORMATION: N-terminus of Lys at position 1 is acetylated
<220> FEATURE:
<221> NAME/KEY: MOD_RES
<222> LOCATION: 12
<223> OTHER INFORMATION: C-terminus of Arg at position 12 is amidated

<400> SEQUENCE: 1

Lys Leu Arg Pro Val Ala Met Val Arg Pro Val Arg
1               5                   10

<210> SEQ ID NO 2
<211> LENGTH: 24
<212> TYPE: PRT
<213> ORGANISM: Artificial Sequence
<220> FEATURE:
<223> OTHER INFORMATION: Sequence of the Hippo signaling pathway
      inhibitor BI-107F9
<220> FEATURE:
<221> NAME/KEY: MOD_RES
<222> LOCATION: 1
<223> OTHER INFORMATION: N-terminus of Gly at position 1 is acetylated
<220> FEATURE:
<221> NAME/KEY: MOD_RES
```

-continued

```
<222> LOCATION: 24
<223> OTHER INFORMATION: C-terminus of Arg at position 24 is amidated

<400> SEQUENCE: 2

Gly Arg Lys Lys Arg Arg Gln Arg Arg Pro Gln Lys Leu Arg
1               5                   10                  15

Pro Val Ala Met Val Arg Pro Val Arg
            20

<210> SEQ ID NO 3
<211> LENGTH: 21
<212> TYPE: DNA
<213> ORGANISM: Artificial Sequence
<220> FEATURE:
<223> OTHER INFORMATION: Forward primer for amplification of the human
      cyclophilin A locus

<400> SEQUENCE: 3
catctgcact gccaagactg a                                              21

<210> SEQ ID NO 4
<211> LENGTH: 22
<212> TYPE: DNA
<213> ORGANISM: Artificial Sequence
<220> FEATURE:
<223> OTHER INFORMATION: Reverse primer for amplification of the human
      cyclophilin A locus

<400> SEQUENCE: 4
ttcatgcctt ctttcacttt gc                                             22

<210> SEQ ID NO 5
<211> LENGTH: 19
<212> TYPE: DNA
<213> ORGANISM: Artificial Sequence
<220> FEATURE:
<223> OTHER INFORMATION: Forward primer for amplification of the human
      TAZ locus

<400> SEQUENCE: 5
gtatcccagc caaatctcg                                                 19

<210> SEQ ID NO 6
<211> LENGTH: 18
<212> TYPE: DNA
<213> ORGANISM: Artificial Sequence
<220> FEATURE:
<223> OTHER INFORMATION: Reverse primer for amplification of the of the
      human TAZ locus

<400> SEQUENCE: 6
ttctgagtgg ggtggttc                                                  18

<210> SEQ ID NO 7
<211> LENGTH: 20
<212> TYPE: DNA
<213> ORGANISM: Artificial Sequence
<220> FEATURE:
<223> OTHER INFORMATION: Forward primer for amplification of the human
      YAP1 locus

<400> SEQUENCE: 7
gtgagcccac aggagttagc                                                20

<210> SEQ ID NO 8
<211> LENGTH: 20
```

```
<212> TYPE: DNA
<213> ORGANISM: Artificial Sequence
<220> FEATURE:
<223> OTHER INFORMATION: Reverse primer for amplification of the of the
      human YAP1 locus

<400> SEQUENCE: 8
ctcgagagtg ataggtgcca                                              20
```

METHODS OF TREATING RESISTANT CANCERS

CROSS-REFERENCE TO RELATED APPLICATION

This is a national stage application under 35 U.S.C § 371 of international patent application PCT/US2018/033457, filed May 18, 2018, which claims benefit of priority under 35 U.S.C. § 119(e) of provisional application U.S. Ser. No. 62/507,837 filed May 18, 2017, now abandoned, the entirety of which is hereby incorporated by reference.

GOVERNMENT SUPPORT CLAUSE

This invention was made with government support under grant number(s) CA131074 and CA184027 awarded by the National Institutes of Health. The government has certain rights in the invention.

BACKGROUND OF THE INVENTION

Field of the Invention

The present invention is directed to the field of cancer therapy. More specifically, the present invention is directed to methods for reversing resistance to Rapidly Accelerated Fibrosarcoma kinase (BRAF) inhibitors.

Description of the Related Art

Nearly one-half of metastatic melanoma patients harbor a BRAFV600 mutation, the most common being BRAF (V600E) [1]. These constitutively-active mutants stimulate ERK1/2 and other signaling pathways to drive tumor cell survival (2,3).

Vemurafenib (PLX4032) and dabrafenib are BRAF inhibitors that target BRAFV600-mutant metastatic melanoma and have been shown to improve survival (4). These agents are remarkably effective, but the majority of patients ultimately become resistant (4,5).

Tumor cells utilize a number of strategies to circumvent these inhibitors, including activation of alternate survival pathways (3). Hippo is an important signaling pathway that controls tissue and organ size (6) and is comprised of Mst1/2 kinases that phosphorylate LATS1/2 kinases which phosphorylate the nuclear adaptor factors, YAP1 and TAZ. In proliferating cells, YAP1 and TAZ localize to the nucleus where they interact with TEAD transcription factors to drive cell proliferation and survival. In contrast, activation of LATS1/2 results in YAP1 and TAZ phosphorylation which causes these proteins to relocate to the cytoplasm where they are degraded (6,7) leading to reduced proliferation. Hippo signaling is frequently reduced in tumors leading to enhanced nuclear YAP1/TAZ accumulation and activation of cell proliferation (6,8).

In melanoma, reduced Hippo pathway signaling is associated with enhanced tumor formation and metastasis (9-11). Recent reports (12,13) identify YAP1/TAZ as BRAF inhibitors resistance factors in melanoma. These studies suggest that BRAF inhibitor treatment promotes remodeling of the cytoskeleton that promotes nuclear accumulation and activation of YAP1/TAZ (13). This concept is consistent with the known activation of YAP1 in response to cytoskeletal changes (14). An additional study suggests that YAP1 confers apoptosis resistance by increasing BCL-XL expression (12).

Overall, there is a deficiency in the art for optimal methods that can reverse resistance to BRAF inhibitors in cancer treatments. The present invention fulfills this long-standing need and desire in the art.

SUMMARY OF THE INVENTION

The present invention is directed to a method of reducing resistance in an individual having a drug resistant cancer comprising the step of administering to the individual a pharmacologically effective dose of a Hippo signaling pathway inhibitor. The present invention is directed to a related method comprising the further step of administering to the individual a BRAF inhibitor.

The present invention also is directed to a method of reducing resistance in an individual with a BRAF inhibitor resistant cancer, comprising the step of administering to the individual a Hippo signaling pathway inhibitor. The present invention is directed to a related method comprising the further step of administering to the individual a BRAF inhibitor.

The present invention is directed further to a method of treating an individual having a BRAF inhibitor resistant cancer or at risk for developing BRAF inhibitor resistance, comprising the step of administering to the individual a pharmacologically effective dose of Verteporfin and a pharmacologically effective dose of a BRAF inhibitor.

The present invention is directed further still to a method of treating an individual having a malignant melanoma comprising the steps of administering to the individual a pharmacological composition comprising a Hippo signaling pathway inhibitor and a BRAF inhibitor.

BRIEF DESCRIPTION OF THE DRAWINGS

FIGS. 1A-1I show that YAP1 and TAZ levels are elevated in A375-PLX-R cells and confer resistance to PLX4032. FIG. 1A shows the effect of BRAF inhibitor, PLX4032 (vemurafenib) on proliferation of BRAF inhibitor sensitive A375 cells and BRAF inhibitor resistant A375-PLX-R cells. FIG. 1B shows YAP1, TAZ and TEAD levels in A375 and A375-PLX-R cells following treatment with 1 µM PLX4032 for 24 h. FIG. 1C shows that the increase in YAP1 and TAZ levels in A375-PLX-R cells is not due to a change in YAP1 or TAZ mRNA. FIG. 1D shows that treatment with PLX4032 or YAP1-siRNA reduces A375 cell proliferation, and that expression of constitutively active YAP1, YAP (S127A), reverses PLX4032-dependent growth suppression. FIG. 1E shows that YAP1 knockdown reduces growth and restores sensitivity of A375-PLX-R cells to PLX4032. FIG. 1F shows that treatment with PLX4032 or TAZ-siRNA reduces A375 cell proliferation, and that expression of constitutively active TAZ, TAZ(S89A), partially reverses the PLX4032-dependent growth suppression. FIG. 1G shows that TAZ knockdown reduces growth and restores sensitivity of A375-PLX-R cells to PLX4032. FIG. 1H confirms successful knockdown and overexpression of YAP1 (supports FIGS. 1D and 1E). FIG. 1I confirms successful knockdown and overexpression of TAZ (supports FIGS. 1F and 1G).

FIG. 2A shows in graphical form that PLX4032 treatment suppresses A375 cell spheroid formation, but not A375-PLX-R cell spheroid formation. FIG. 2B is a photomicrograph of spheroid formation showing that PLX4032 treatment suppresses spheroid formation in A375 cells, but not A375-PLX-R cells. FIG. 2C shows that A375-PLX-R cell-derived melanoma cancer stem (MCS) cells express elevated YAP1, TAZ and TEAD levels as compared to A375 cell derived MCS cells. FIG. 2D is an immunofluorescence photomicrograph showing that there was no significant change in YAP1 or TAZ subcellular distribution in control versus PLX4032-treated A375 cells (panel "C" is negative control for antibody staining). FIG. 2E shows that A375-PLX-R cell invasion is enhanced by 50% compared to A375 cells, and that the invasion is not suppressed by PLX4032 in either cell type. FIG. 2F shows that although YAP1 knockdown reduces invasion, PLX4032 treatment is without effect suggesting that YAP1 knockdown does not sensitize the cells to PLX4032 with respect to matrigel invasion. FIG. 2G shows that although TAZ knockdown reduces invasion, PLX4032 treatment is without effect suggesting that TAZ knockdown does not sensitize the cells to PLX4032 with respect to matrigel invasion.

FIG. 3A shows the effects of BRAF inhibitor treatment in A375 cells. BRAF inhibitor treatment reduces ERK1/2 activity, reduced cyclin B and cyclin A, and increased p21Cip1 and p27. PLX4032 treatment also enhanced apoptosis as measured by increased accumulation of cleaved PARP and reduced levels of pro-caspase 8 and 9. Consistent with a role for YAP1 in attenuating PLX4032 action, these changes are reversed by expression of constitutively active forms of YAP1 (YAP (S127A)). FIG. 3B shows the effects of BRAF inhibitor treatment in A375 cell. BRAF inhibitor treatment reduces ERK1/2 activity, reduced cyclin B and cyclin A, and increased p21Cip1 and p27. PLX4032 treatment also enhanced apoptosis as measured by increased accumulation of cleaved PARP and reduced levels of procaspase 8 and 9. Consistent with a role for YAP1 in attenuating PLX4032 action, these changes are reversed by expression of constitutively active forms of TAZ (TAZ(S89A)). FIG. 3C shows that YAP(S127A) expression reverses PLX4032 suppression of A375 cell proliferation. FIG. 3D shows invasion of PLX4032 sensitive cells into matrigel. FIG. 3E shows invasion of PLX4032 resistant cells into matrigel. FIG. 3F shows that ERK1/2 phosphorylation is reduced in PLX4032-treated A375 cells in the presence or absence of TEADs but in contrast, ERK1/2 activity is only reduced in A375-PLX-R cells following TEAD knockdown and PLX4032 treatment.

FIGS. 4A-4I show that verteporfin suppression of spheroid formation and invasion is associated with reduced YAP1/TAZ level. FIG. 4A shows that verteporfin treatment suppresses A375 spheroid formation by 50% at verteporfin concentrations as low at 0.1-0.25 µM and that spheroid formation is nearly completely inhibited at higher verteporfin concentrations. FIG. 4B shows that verteporfin treatment suppresses A375-PLX-R spheroid formation by 50% at verteporfin concentrations as low at 0.1-0.25 µM and that spheroid formation is nearly completely inhibited at higher verteporfin concentrations. FIG. 4C shows that 20 µM verteporfin treatment reduces spheroid number/integrity by 30-50% after a 3-day treatment. FIG. 4D shows that matrigel invasion is 50% suppressed at concentrations of 0.5-1 µM verteporfin in A375 cells and that suppression is nearly complete at higher concentrations. FIG. 4E shows that matrigel invasion is 50% suppressed at concentrations of 0.5-1 µM verteporfin in A375-PLX-R cells and that suppression is nearly complete at higher concentrations. FIG. 4F shows that verteporfin treatment does not impact the level of YAP1 or TAZ mRNA. FIG. 4G shows that verteporfin treatment reduce YAP1 and TAZ protein levels. FIG. 4H shows that verteporfin treatment reduces TEAD transcription factor level in A375 and A375-PLX-R cells. FIG. 4I shows that verteporfin-dependent reduction in YAP1, TAZ and TEAD levels is not reversed by the proteasome inhibitor, lactacystin.

FIG. 5A shows that treatment with 0-1 µM PLX4032 does not suppress A375-PLX-R spheroid formation, but that co-treatment with 0.1 µM verteporfin restores PLX4032 suppression of spheroid number. FIG. 5B shows that PLX4032 treatment does not reduce spheroid formation in BRAF-resistant (PLX-R) cells. FIG. 5C shows that PLX4032 treatment does not reduce invasion in BRAF-resistant (PLX-R) cells. FIG. 5D shows that YAP1, TAZ and TEAD levels are markedly increased in BRAF-resistant (PLX-R) cells. FIG. 5E shows that verteporfin treatment reduces spheroid formation in BRAF-resistant (PLX-R) cells. FIG. 5F shows that verteporfin treatment reduces matrigel invasion in BRAF-resistant (PLX-R) cells. FIG. 5G shows that forced expression of YAP(S127A) or TAZ(S89A) partially reverses PLX4032 suppression of cell growth. FIG. 5H shows that treatment of the BRAF-resistant cells A375-PLX-R with SCH772984, a specific inhibitor of ERK1/2 produced a time-dependent reduction in cell number. FIG. 5I shows that treatment of the BRAF-resistant cells A375-PLX-R with SCH772984, a specific inhibitor of ERK1/2 reduces proliferation of SKMEL5-PLX-R, SKMEL28-PLX-R and WM3248-PLX-R cells.

FIG. 6A shows that A375-PLX-R derived MCS cells form large tumors compared to A375 MCS cells. FIG. 6B shows that PLX4032 suppresses growth of A375 but not A375-PLX-R spheroid cell-derived tumors. FIG. 6C shows that A375-PLX-R spheroid cell-derived tumors express elevated levels of YAP1, TAZ and TEADs as compared to A375 spheroid cell-derived tumors. FIG. 6D shows that verteporfin treatment reduced tumor volumes. FIG. 6E shows a representative image of a tumor without and with verteporfin treatment. FIG. 6F shows that reduction in tumor volume following verteporfin treatment corresponds to suppression of YAP1 and TAZ levels. FIG. 6G shows that tumor-derived A375-PLX-R cells invade matrigel nearly three times as efficiently as tumor-derived A375 cells, and that in vivo PLX4032 treatment does not suppress matrigel invasion of sensitive or resistant cells. FIG. 6H shows that in contrast to the data in FIG. 6G, verteporfin treatment of tumors reduces tumor formation and yields a cell population with reduced matrigel invasion.

FIG. 7A shows that in the absence of verteporfin, PLX4032 does not suppress A375-PLX-R tumor formation. FIG. 7B shows representative images tumors from animals treated without and with verteporfin. FIG. 7C shows reduction in YAP1, YAP1-P, TAZ and TEAD levels in tumor lysates obtained from control and treated animals.

DETAILED DESCRIPTION OF THE INVENTION

Figure 1A:
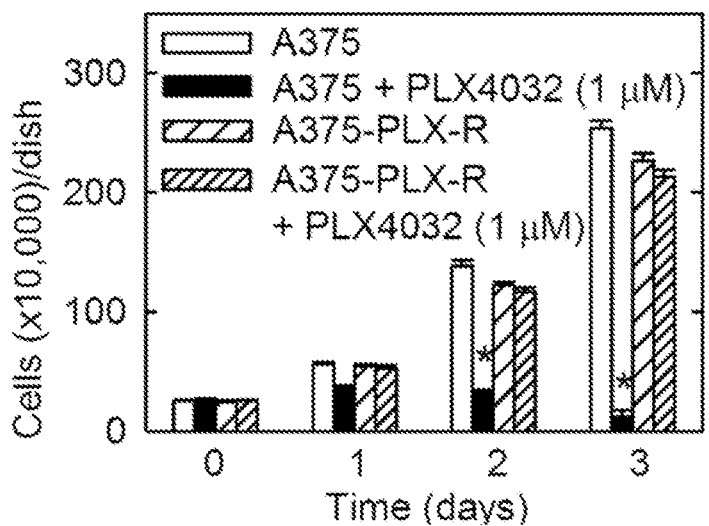

Certain terms employed in the specification, examples and appended claims are defined herein. These definitions should be read in light of the remainder of the disclosure and understood as by a person of ordinary skill in the art. Unless defined otherwise, all technical and scientific terms used herein have the same meaning as commonly understood by a person of ordinary skill in the art.

The articles "a" and "an" when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, components, method steps, and/or methods of the invention. It is contemplated that any composition, component or method described herein can be implemented with respect to any other composition, component or method described herein.

The term "or" in the claims refers to "and/or" unless explicitly indicated to refer to alternatives only or the alternatives are mutually exclusive, although the disclosure supports a definition that refers to only alternatives and "and/or".

The terms "comprise" and "comprising" are used in the inclusive, open sense, meaning that additional elements may be included.

The term "including" is used herein to mean "including, but not limited to". "Including" and "including but not limited to" are used interchangeably.

The term "cancer" is used herein to mean a primary tumor, a metastasized tumor, cancer stem cells including, any homogenous or heterogenous combinations of these.

In one embodiment of the present invention, there is provided a method for reducing resistance in an individual having a drug resistant cancer. This method comprises the step of administering to the individual a pharmacologically effective dose of a Hippo signaling pathway inhibitor. In this embodiment, the drug resistant cancer includes, but is not limited to melanoma, colorectal cancer, cholangiocarcinoma, thyroid cancer, lung cancer, non-small-cell lung cancer, multiple myeloma, breast cancer, cervical cancer, ovarian cancer, gastric cancer, brain tumor, head and neck tumor, esophageal cancer, biliary tract cancer, pancreatic cancer, sarcoma, prostate cancer and testicular cancer.

In this embodiment, the Hippo signaling pathway inhibitor is an inhibitor of the transcriptional regulators Yes-associated protein 1 (YAP1) or Transcriptional Coactivator with PDZ-binding motif (TAZ) or a Transcription enhancer domain (TEAD) inhibitor and may inhibit at the transcriptional level, translational level or, post-translational level. These inhibitors may be reversible or irreversible inhibitors and may block the Hippo signaling pathway through competitive inhibition, uncompetitive inhibition, or non-competitive inhibition, or may promote degradation or post-translational modification of proteins of the Hippo signaling pathway. Alternatively, the Hippo signaling pathway inhibitor may inhibit an activating step upstream of YAP1 and TAZ. An example of a Hippo signaling pathway inhibitor is Verteporfin. Alternatively, representative examples of Hippo signaling pathway inhibitors include, but are not limited to, Protoporphyrin IX, Zoledronic acid, Super-TDU, Auranofin, Metformin, Ivermectin and Milbemycin-D, Latrunculin A, Okadaic acid, Simvastatin, Staurosporine, Clomipramine, Heclin Dasatinib, Wortmannin, 4-((4-(3,4-Dichlorophenyl)-1,2,5-thiadiazol-3-yl)oxy)butane-1-ol, 4-[2-[4-(4-Hydroxyphenyl)butan-2-ylamino]ethyl]benzene-1,2-diol (Dobutamine), 4-[(1R)-1-Hydroxy-2-(methylamino)ethyl]benzene-1,2-diol (Epinephrine), 5-(2-phenylpyrazolo[1,5-a]pyridin-3-yl)-2H-pyrazolo[3,4-c]pyridazin-3-amine, 4-{[(1S)-1-Carboxy-3-methylbutyl]carbamoyl}-N-[(1H-imidazol-4-yl)methyl]-3-(naphthalen-trifluoroacetate, 2-[4-(Trifluoromethyl)phenyl]-1,5,7,8-tetrahydrothiopyrano[4,3-d]pyrimidin-4-one, 4-[(1R)-1-aminoethyl]-N-pyridin-4-ylcyclohexane-1-carboxamide, Ac-KLRPVAMVRPVR-NH$_2$ (SEQ ID NO: 1), or Ac-GRKKRRQRRRPQKLRPVAMVRPVR-NH$_2$ (SEQ ID NO: 2) (39). These inhibitors are well known in the art and one of ordinary skill may readily select and use these for the purpose of practicing the method claimed in this invention. The Hippo signaling pathway inhibitor may be administered at a dosage of about 1 mg/kg to about 500 mg/kg, preferably about 1 mg/kg to about 100 mg/kg, more preferably about 1 mg/kg to about 50 mg/kg, and most preferably about 1 mg/kg to about 10 mg/kg.

Further to this embodiment, the method comprises administering to the individual having the drug resistant cancer a BRAF inhibitor. Any commercially available BRAF inhibitor may be used for this purpose, including those being used presently in the clinic as a treatment modality for cancer. Examples of such BRAF inhibitors are vemurafenib, dabrafenib or encorafenib. Alternative representative examples of BRAF inhibitors include, but are not limited to, methyl N-[6-[2-(5-chloro-2-methylphenyl)-1-hydroxy-3-oxoisoindol-1-yl]-1H-benzimidazol-2-yl] carbamate (BMS-098662), PLX3603, PLX4720 RAF265, and Sorafenib Tosylate (40). One of ordinary skill in this art would be capable of selecting these and similar inhibitors, and use them for the intended purpose as claimed, and further select a suitable dosage depending on the type of cancer being targeted. Preferably the BRAF inhibitor may be administered at a dosage range of about 1 mg/kg to about 500 mg/kg, preferably about 1 mg/kg to about 100 mg/kg, more preferably about 1 mg/kg to about 50 mg/kg, and most preferably about 2 mg/kg to about 20 mg/kg.

Also in this embodiment, the Hippo signaling pathway inhibitor and the BRAF inhibitor may be administered by an oral route or any parenteral route including, but not limited to, intravenous, intraperitoneal, subcutaneous, intradermal, intramuscular, epidural and intrathecal. In addition, the inhibitors may be administered sequentially or concurrently one or more times per day on a daily schedule, every other day, a weekly schedule, or a monthly schedule. In one aspect, the inhibitors may be administered concurrently wherein, the BRAF inhibitors is administered orally and the Hippo signaling pathway inhibitor is administered intraperitoneally.

In another embodiment of the present invention, there is provided a method of reducing resistance in an individual with a BRAF inhibitor resistant cancer. The method comprises, administering to the individual, a Hippo signaling pathway inhibitor. In this embodiment, the BRAF inhibitor resistant cancer has any of the mutation in the BRAF protein including, but not limited to, BRAFV600, BRAFR461, BRAF1462, BRAFG463, BRAFG463, BRAFG465, BRAFG465, BRAFG468, BRAFN580, BRAFE585, BRAFD593, BRAFF594, BRAFG595, BRAFL596, BRAFT598, BRAFV599, BRAFA727 or any combinations of these mutations. For example, the mutation may be a BRAFV600 mutation, wherein the valine at position 600 on the protein sequence is replace with a glutamate (BRAFV600E), lysine (BRAFV600K), aspartate (BRAFV600D) or arginine (BRAFV600R). Such a BRAF inhibitor resistant cancer include, but is not limited to, melanoma, colorectal cancer, cholangiocarcinoma, thyroid cancer, lung cancer, non-small-cell lung cancer, multiple myeloma, breast cancer, cervical cancer, ovarian cancer, gastric cancer, brain tumor, head and neck tumor, esophageal cancer, biliary tract cancer, pancreatic cancer, sarcoma, prostate cancer, or testicular cancer.

In this embodiment, the Hippo signaling pathway inhibitor may be an inhibitor of either of the transcriptional regulators Yes-associated protein 1 (YAP1), a Transcriptional Coactivator with PDZ-binding motif (TAZ) or an inhibitor of Transcription enhancer domain (TEAD) and may inhibit at the transcriptional level, translational level or, post-translational level. These inhibitors may be reversible or irreversible inhibitors and may block the Hippo signaling pathway through competitive inhibition, uncompetitive inhibition, or non-competitive inhibition, or may promote degradation or post-translational modification of proteins of the Hippo signaling pathway. Alternatively, the Hippo signaling pathway inhibitor may inhibit an activating step upstream of YAP1 and TAZ. Examples of Hippo signaling pathway inhibitors include but are not limited to, Verteporfin, Protoporphyrin IX, Zoledronic acid, Super-TDU, Auranofin, Metformin, Ivermectin and Milbemycin-D, Latrunculin A, Okadaic acid, Simvastatin, Staurosporine, Clomipramine, Heclin Dasatinib, Wortmannin, 4-((4-(3,4-Dichlorophenyl)-1,2,5-thiadiazol-3-yl)oxy)butane-1-ol, 4-[2-[4-(4-Hydroxyphenyl)butan-2-ylamino]ethyl]benzene-1,2-diol (Dobutamine), 4-[(1R)-1-Hydroxy-2-(methylamino)ethyl]benzene-1,2-diol (Epinephrine), 5-(2-phenylpyrazolo[1,5-a]pyridin-3-yl)-2H-pyrazolo[3,4-c]pyridazin-3-amine, 4-{[(1S)-1-Carboxy-3-methylbutyl]carbamoyl}-N-[(1H-imidazol-4-yl)methyl]-3-(naphthalen-trifluoroacetate, 2-[4-(Trifluoromethyl)phenyl]-1,5,7,8-tetrahydrothiopyrano[4,3-d]pyrimidin-4-one, 4-[(1R)-1-aminoethyl]-N-pyridin-4-ylcyclohexane-1-carboxamide, Ac-KLRPVAMVRPVR-NH2 (SEQ ID NO: 1) and Ac-GRKKRRQRRRPQKLRPVAMVRPVR-NH2 (SEQ ID NO: 2) (39). These inhibitors are well known in the art and one of ordinary skill may readily select and use these for the purpose of practicing the method claimed in this invention. The Hippo signaling pathway inhibitor may be administered at a dosage and schedule as described supra.

Further to this embodiment, the method comprises administering a BRAF inhibitor to the individual having the drug resistant cancer. Any commercially available BRAF inhibitor may be used for this purpose, including those being used presently in the clinic as a treatment modality for cancer. Examples of such BRAF inhibitors include, but is not limited to, vemurafenib, dabrafenib and encorafenib, methyl N-[6-[2-(5-chloro-2-methylphenyl)-1-hydroxy-3-oxoisoindol-1-yl]-1H-benzimidazol-2-yl] carbamate (BMS-098662), PLX3603, PLX4720 RAF265, and Sorafenib Tosylate (40). One of ordinary skill in this art would be capable of selecting these and similar inhibitors, and use them for the intended purpose as claimed, and further select a suitable dosage depending on the type of cancer being target. Preferably the BRAF inhibitor may be administered at a dosage and schedule as described supra.

Also in this embodiment, the Hippo signaling pathway inhibitor and the BRAF inhibitor may be administered by oral route or any parenteral route including but not limited to intravenous, intraperitoneal, subcutaneous, intradermal, intramuscular, epidural and intrathecal. In addition the inhibitors may be administered sequentially or concurrently one or more times per day on a daily schedule, every other day, a weekly schedule, or a monthly schedule. In one aspect, the inhibitors may be administered concurrently wherein, the BRAF inhibitors is administered orally and the Hippo signaling pathway inhibitor is administered intraperitoneally.

In yet another embodiment of the present invention, there is provided a method of treating BRAF inhibitor resistance in an individual having a BRAF inhibitor resistant cancer. The method comprises the step of administering to the individual a pharmacologically effective dose of Verteporfin and a pharmacologically effective dose of a BRAF inhibitor.

In this embodiment, the BRAF inhibitor resistant cancer may have a mutation in the BRAF protein including, but not limited to, BRAFV600, BRAFR461, BRAF1462, BRAFG463, BRAFG463, BRAFG465, BRAFG465, BRAFG468, BRAFN580, BRAFE585, BRAFD593, BRAFF594, BRAFG595, BRAFL596, BRAFT598, BRAFV599, BRAFA727 or any combinations of these mutations. For example, the mutation may be a BRAFV600 mutation, wherein the valine at position 600 on the protein sequence is replace with a glutamate (BRAFV600E), lysine (BRAFV600K), aspartate (BRAFV600D) or arginine (BRAFV600R). Such BRAF inhibitor resistant cancers include, but are not limited to melanoma, colorectal cancer, cholangiocarcinoma, thyroid cancer, lung cancer, non-small-cell lung cancer, multiple myeloma, breast cancer, cervical cancer, ovarian cancer, gastric cancer, brain tumor, head and neck tumor, esophageal cancer, biliary tract cancer, pancreatic cancer, sarcoma, prostate cancer, or testicular cancer.

In this embodiment, Verteporfin is administered at a dosage as described supra for Hippo inhibitors. Also in this embodiment, the BRAF inhibitor may comprise any of the commercial BRAF inhibitors, including, but not limited to, BRAF inhibitors identified as a clinical treatment modality. Examples of such BRAF inhibitors include, but are not limited to, those inhibitors as described supra. One of ordinary skill in this art would be capable of selecting these and similar inhibitors, and use them for the intended purpose as claimed, and further select a suitable dosage depending on the type of cancer being target. Preferably the BRAF inhibitor may be administered at a dosage range of about 1 mg/kg to about 500 mg/kg, preferably about 1 mg/kg to about 100 mg/kg, more preferably about 1 mg/kg to about 50 mg/kg, and most preferably about 2 mg/kg to about 20 mg/kg. In addition in this embodiment, Verteporfin and the BRAF inhibitor may be administered by an oral route or any parenteral route including, but not limited to intravenous, intraperitoneal, subcutaneous, intradermal, intramuscular, epidural and intrathecal. Furthermore, the BRAF inhibitor may be administered before, after or with Verteporfin.

In yet another embodiment of the present invention, there is provided a method of treating an individual having a malignant melanoma. The method comprises, administering to the individual a pharmacological composition comprising a Hippo signaling pathway inhibitor and a BRAF inhibitor. In this embodiment, the malignant melanoma may have a BRAFV600 mutation, which may comprise a replacement of the valine at position 600 on the protein sequence with a glutamate (BRAFV600E), lysine (BRAFV600K), aspartate (BRAFV600D) or arginine (BRAFV600R). In one aspect of this embodiment, the malignant melanoma has a BRAFV600E mutation.

Also in this embodiment, the Hippo signaling pathway inhibitor may be an inhibitor of either of the transcriptional regulators Yes-associated protein 1 (YAP1), a Transcriptional Coactivator with PDZ-binding motif (TAZ) or a Transcription enhancer domain (TEAD) inhibitor and may inhibit at the transcriptional level, translational level or, post-translational level. These inhibitors may be reversible or irreversible inhibitors and may block the Hippo signaling pathway through competitive inhibition, uncompetitive inhibition, or non-competitive inhibition, or may promote degradation or post-translational modification of proteins of the Hippo signaling pathway. Alternatively, the Hippo signaling pathway inhibitor may inhibit an activating step upstream of YAP1 and TAZ. Examples of Hippo signaling pathway inhibitors include but are not limited to those inhibitors as described supra. These inhibitors are well known in the art and one of ordinary skill may readily select and use these for the purpose of practicing the method claimed in this invention. The Hippo signaling pathway inhibitor may be administered at a dosage and schedule as described supra.

In addition, the BRAF inhibitor may be any commercial BRAF inhibitors including, but not limited to those used as a clinical treatment modality for melanoma. Examples of such BRAF inhibitors include, but are not limited to, those inhibitors as described supra. One of ordinary skill in this art would be capable of selecting these and similar inhibitors, and use them for the intended purpose as claimed, and further select a suitable dosage depending on the type of cancer being target. Preferably the BRAF inhibitor may be administered at a dosage range between Preferably the BRAF inhibitor may be administered at a dosage of about 1 mg/kg to about 500 mg/kg, preferably about 1 mg/kg to about 100 mg/kg, more preferably about 1 mg/kg to about 50 mg/kg, and most preferably about 2 mg/kg to about 20 mg/kg. Furthermore in this embodiment, Verteporfin and the BRAF inhibitor may be administered by oral route or any parenteral route including but not limited to intravenous, intraperitoneal, subcutaneous, intradermal, intramuscular, epidural and intrathecal. Further still, the BRAF inhibitor is administered before, after or with Verteporfin.

The following examples are given for the purpose of illustrating various embodiments of the invention and are not meant to limit the present invention in any fashion.

EXAMPLE 1

Materials and Methods
Antibodies and Reagents

Sodium pyruvate (11360-070), Dulbecco's Modified Eagle's Medium (DMEM) (11960-077), 0.25% trypsin-EDTA (25200-056) and L-Glutamine (25030-164) were purchased from Gibco (Grand Island, N.Y.). Heat inactivated fetal calf serum (FCS, F4135), anti-b-actin (A5441) and lactacystin (L6785) were purchased from Sigma (St. Louis, Mo.). Cell lysis Buffer (9803) and antibodies for ERK1/2 (9102) ERK1/2-P (9101), YAP1 (4912), YAP1-P (13008), TAZ (4883) pan-TEAD (13295), p21$^{Cip1}$ (2947), cleaved PARP (9541), caspase-8 (9746) and caspase-9 (9502) were from Cell Signaling Technologies (Danvers, Mass.). Antibodies to cyclin A (SC-751), cyclin B (SC-245) p27 (SC-1641) and TAZ-P (SC-17610-R) were purchased from Santa Cruz (Dallas, Tex.). YAP1 (52771) antibody for immunofluorescence was purchased from Abcam (Cambridge, Mass.). YAP1-siRNA (S102662954, S104438651, S104438644, S104438637) were purchased from Qiagen (Valencia, Calif.). Control- (37007) and TAZ-siRNA (36568) were purchased from Santa Cruz. TEAD1 (M-012603-01-0005), TEAD2 (M-012611-00-0005), TEAD3 (M-012604-01-0005) and TEAD4-siRNA (M-019570-03-0005) were purchased from Dharmacon. YAP(S127A) (27370) and TAZ(S89A) (32840) plasmids were obtained from Addgene (Cambridge, Mass.). PLX4032 (RG7204) was purchased from APExBIO (Houston Tex.). Peroxidase-conjugated anti-mouse IgG (NXA931) and anti-rabbit IgG (NA934V) were obtained from GE healthcare (Buckinghamshire, UK). Alexaflour 555 (A21424) and Alexaflour 488 (A11034) were purchased from Invitrogen. DAPI (D9542) was purchased from Sigma. Paraformaldehyde (15713) was purchased from Electron Microscopy Sciences (Hatfield, Pa.). Matrigel (354234) and BD Biocoat cell inserts (353097) were purchased from BD Biosciences. Verteporfin (5305) was from Tocris Bioscience (Bristol, UK). Lab-Tek II Chamber Slides (154526) were from Nunc (Rochester, N.Y.). LAB-TEKII chamber slides (154526) were purchased from Thermo-Fisher (Waltham, Mass.). A375, SK-MEL-5, SK-MEL-28 and WM3248 cells, which harbor the BRAF(V600E) mutation, were provided by Dr. David Kaetzel (Biochemistry and Molecular Biology, University of Maryland School of Medicine). YAP1 mutant plasmids were provided by John Lamar/Richard Hynes (8). These include YAP(S127A), YAP(S127A)(S94A), YAP (S127A)(WW1), YAP(S127A)(WW2), YAP(S127A) (WW1/WW2), YAP(S127A)(Dbl) and YAP(S127A) (PDZbm) (8). The ERK1/2 inhibitor, SCH772984, was obtained from Selleckchem (Houston, Tex., S7101). Data analysis used the student's t-test and values are presented as mean±SEM.

Immunoblotting

Equivalent amounts of protein were electrophoresed on denaturing and reducing 10% polyacrylamide gels and transferred to nitrocellulose membrane. The membrane was blocked by 5% nonfat dry milk for one hour and incubated with 1:1000 primary antibody in 5% nonfat dry milk. Blots were rinsed in TBS-T and then incubated with secondary antibodies (1:5000) for 2 h. Secondary antibody binding was visualized using ECL Prime (Amersham) chemiluminescence detection technology. For immunostaining, cells were harvested, suspended in growth medium, and plated in LAB-TEK II Chamber Slide System. After 24 h, the cells were fixed with 4% paraformaldehyde at room temperature for 15 min, washed three with phosphate-buffered saline, in 0.1% Triton X-100 for 15 min, washed with phosphate-buffered saline, and blocked for 1 h with phosphate-buffered saline containing 7.5% fetal calf serum. Primary antibodies were added, and the slides incubated overnight at 4° C. Cells were then washed three times with phosphate-buffered saline and incubated 1 h with the appropriate Alexa Flour fluorescence probe-conjugated secondary antibody. After additional washing, the cells were stained with DAPI for 10 min prior to imaging.

Spheroid Formation Assay

Cancer cells were maintained under attached conditions in growth media containing DMEM (Invitrogen, Frederick, Md.) supplemented with 4.5 mg/ml D-glucose, 200 mM L-glutamine, 100 mg/ml sodium pyruvate, and 5% fetal calf serum. For spheroid culture, monolayer cultures were dissociated with 0.25% trypsin and the cells were collected by centrifugation, and resuspended in spheroid media, consisting of DMEM/F12 (1:1) (DMT-10-090-CV, Mediatech INC, Manassa, Va.) containing 2% B27 serum-free supplement (17504-044, Invitrogen, Frederick, Md.) 20 ng/ml EGF (E4269, Sigma, St. Louis), 0.4% bovine serum albumin (B4287, Sigma) and 4 mg/ml insulin (19278 Sigma, St. Louis, Mo.) and plated at 40,000 cells per 9.6 cm$^2$ well in six well ultra-low attachment Costar cluster dishes (4371, Corning, Tewksbury, Mass.). Parallel cultures were plated in spheroid media on conventional plastic dishes for growth as monolayer cultures.

Electroporation of Nucleic Acids

Cancer cells (150,000) were plated on 60 mm plates in growth medium. After 24 h, when approximately 50% confluent, the cells were collected using 0.25% trypsin, centrifuged at 200×g, washed with sterile PBS (pH 7.5), suspended in 100 ml of nucleofection reagent R VCA-1001 (Walkersville, Md.) and electroporated with plasmids or siRNA. The cell suspension, containing either 3 µg of siRNA or 2 µg of plasmid DNA was gently mixed and electroporated using the X-001 setting on the AMAXA Electroporator. Immediately after electroporation, pre-warmed media was added, and the suspension was transferred to a 60 mm cell culture plate and adjusted to a final volume of 4 ml with media. Cells were electroporated a second time, following the same protocol, 72 h after the initial electroporation.

Invasion Assay

Matrigel (BD Biolabs) was diluted in 0.01 M Tris-HCL/ 0.7% NaCl, filter-sterilized and 0.1 ml was used to cover the membrane in BD BioCoat cell inserts (#353097, 8 mm pores, 24 well format, membrane growth area=0.33 cm$^2$). Cells 25,000/well were plated in 100 ml of growth media containing 1% FCS atop the Matrigel. Growth media containing 10% FCS was added to the lower well and cells were incubated overnight at 37 C. The following day, excess cells from the top side of the membrane were removed with a cotton swab, and the membrane was rinsed in phosphate-buffered saline, fixed with 4% paraformaldehyde for 10 minutes, washed and stained in 1 mg/ml DAPI for 10 minutes to visualize the cells. The underside of the membrane was photographed with an inverted fluorescent microscope to count the number of cells that had migrated through the Matrigel layer (38).

PLX4032 Resistant Lines

A375, SK-MEL-5 and SK-MEL-28 cell lines were maintained in DMEM growth medium containing 10% FCS, 2 mM L-glutamine and 1 mM sodium pyruvate. The WM3248 cells were maintained in MCDB153:L15 (4:1) growth medium containing 2% FCS, 5 mg/ml insulin and 1.68 mM CaCl$_2$. To create PLX4032-resistant cells, A375, SK-MEL-5, SK-MEL-28 and WM3248 cells were treated with 1 mM PLX4032 in monolayer culture in growth medium for several weeks. The surviving cells were then expanded and cultured in increasing doses of PLX4032 up to 4 mM. The resulting PLX4032-resistant cells, designated PLX4032-resistant (e.g., A375-PLX-R) were routinely maintained in the presence of 1 mM PLX4032.

Tumor Xenograft Assays

Cells were grown for ten days as spheroids and a single cell suspension, prepared by trypsin digestion, was resuspended in phosphate buffered saline containing 30% Matrigel and 100 µl containing 0.1 million cells were injected subcutaneously at the two front flanks of NOD/scid/IL2 receptor gamma-knockout mice (NSG mice) using a 26.5 gauge needle. PLX4032 was dissolved in phosphate-buffered saline containing 10% DMSO and delivered at 20 mg/kg by oral gavage in 100 ml three times per week (M/W/F). Verteporfin was dissolved in phosphate-buffered saline containing 10% DMSO and 0-100 mg/kg was delivered by intraperitoneal injection of 100 ml three times per week (M/W/F). Five mice were used per group (two tumors per mouse) and treatment was initiated two days after tumor cell injection. Tumor growth was monitored by measuring tumor diameter and calculating tumor volume using the formula, volume=$4/3\pi\times$(diameter/2)$^3$. Mice were euthanized by injection of 250 µl of a 2.5% stock of Avertin per mouse followed by cervical dislocation of the neck. Tumor samples were harvested to prepare extract for immunoblot and sections for immunostaining. These experiments were reviewed and approved by the University of Maryland-Baltimore Institutional Animal Care and Use Committee. The plotted values are mean±SEM and significance were determined using the students t-test.

Matrigel Invasion of Tumor-Derived Cells

Tumors were initiated and treated with PLX4032 or verteporfin as above. At 4 weeks, the tumors were removed, mechanically dissociated and dispersed as single cell suspensions with 0.25% trypsin for 10 min and plated as monolayer cultures. After 24 h, the cells were harvested and seeded at 25,000 cells/well atop a 0.1 ml matrigel layer in Millicell (1 cm diameter, 8 mm pore size) chambers in the presence of a serum gradient (38). After 18 h, the membranes were stained with DAPI and the nuclei of migrated cells were visualized by inverted fluorescence microscopy (38).

qRT-PCR Analysis of mRNA Level

Total RNA was isolated using Illustra RNAspin mini kit (GE Healthcare), and 1 µg of RNA was used for cDNA synthesis. Gene expression was measured by real time PCR using Light Cycler 480 SYBR Green I Master Mix (04-707 516 001) from Roche Diagnostics (Indianapolis, Ind.). The signals were normalized using cyclophilin A control primers. The gene specific primers used for detection of mRNA levels were as follows: cyclophilin A (forward, 5'-CATCTGCACTGCCAAGACTGA (SEQ ID NO: 3); reverse, 5'-TTCATGCCTTCTTTCACTTTGC (SEQ ID NO: 4)), TAZ (forward, 5'-GTATCCCAGCCAATC TCG (SEQ ID NO: 5); reverse, 5'-TTCTGAGTGGGGTGGTTC (SEQ ID NO: 6)) and YAP1 (forward, 5'-GTGAGCC-CACAGGAGTTAGC (SEQ ID NO: 7); reverse, 5'-CTCGAGAGTGATAGGTGCCA, (SEQ ID NO: 8)) (11).

EXAMPLE 2

YAP1 and TAZ are BRAF Inhibitors Resistance Factors

Figure 1B:
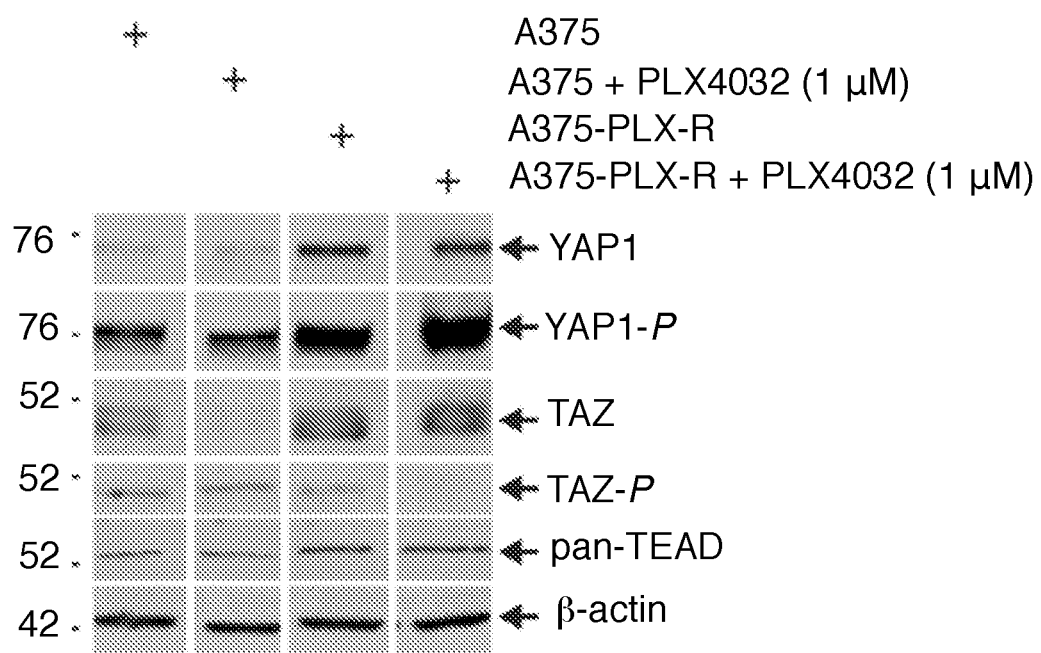
Figure 1C:
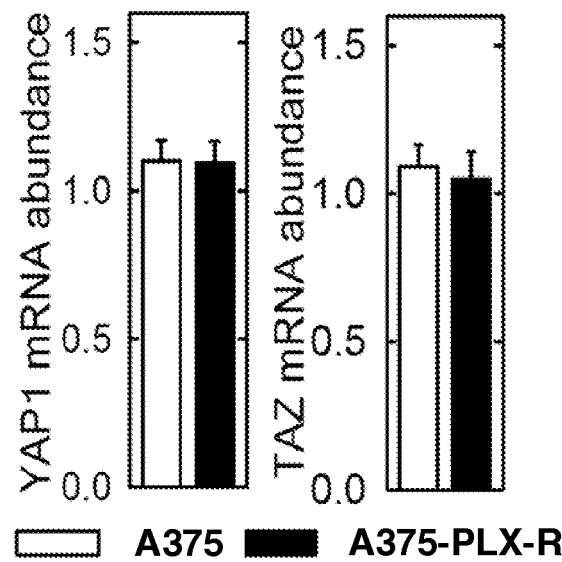

PLX4032 is an important BRAF(V600E)-targeting drug used for the treatment of melanoma that is commercially available as vemurafenib (4). PLX4032 is highly effective in the short-term, but the tumors eventually become resistant (4, 19). As models to study PLX4032 drug resistance, BRAF(V600E)-positive/PLX4032-sensitive A375 cells were used and created PLX4032-resistant cells (e.g., A375-PLX-R) were created by selection in PLX4032 containing medium. FIG. 1A shows that, unlike A375 cells, proliferation of A375-PLX-R cells is not suppressed by PLX4032. To understand the mechanism of resistance, the YAP1 and TAZ transcription adaptor proteins and the TEAD transcription factors were confirmed to have a role in drug resistance (12,13,20-24). FIG. 1B shows that YAP1, TAZ and TEAD levels are increased in A375-PLX-R cells and that the increase in YAP1 level is associated with an increase in apparent YAP1 phosphorylation. FIG. 1C shows that the YAP1 and TAZ increase is not due to a change in YAP1 or TAZ mRNA level.

Figure 1D:
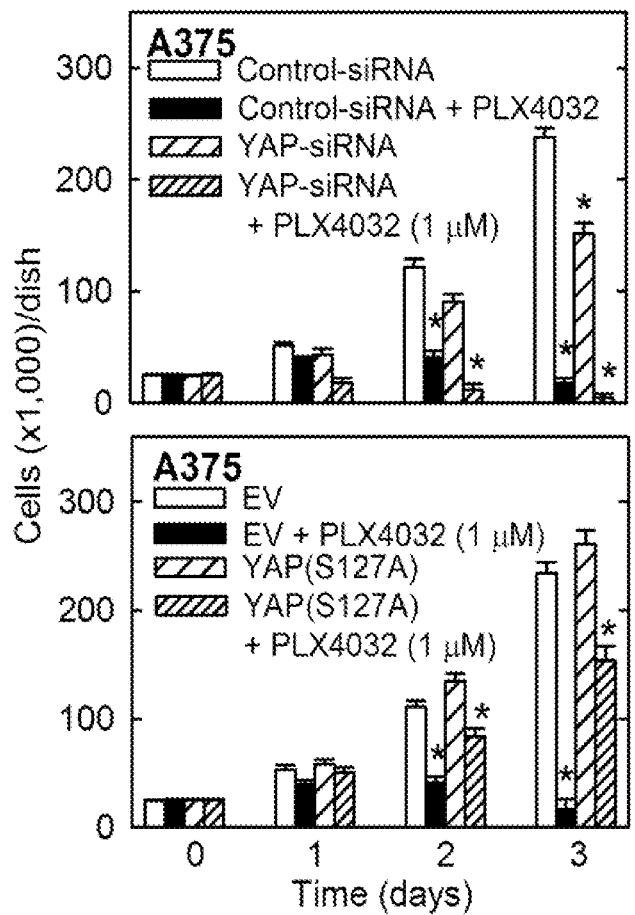
Figure 1E:
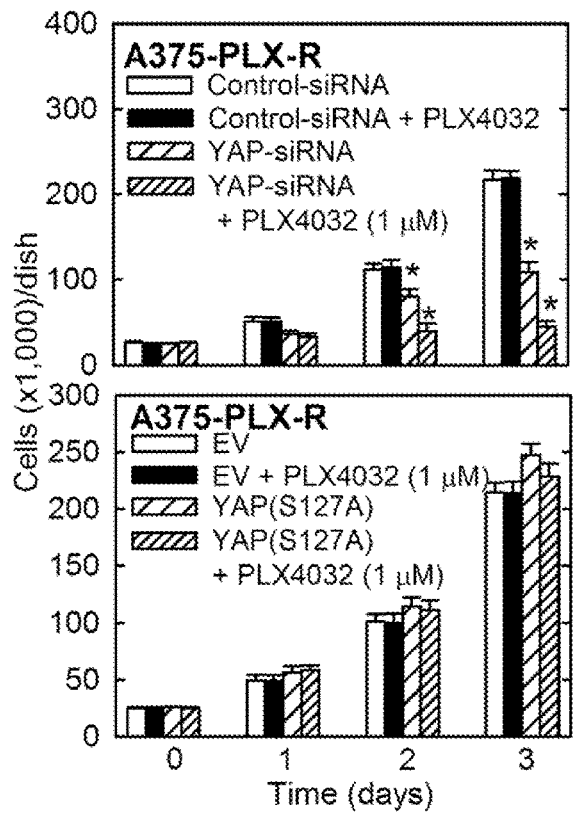
Figure 1F:
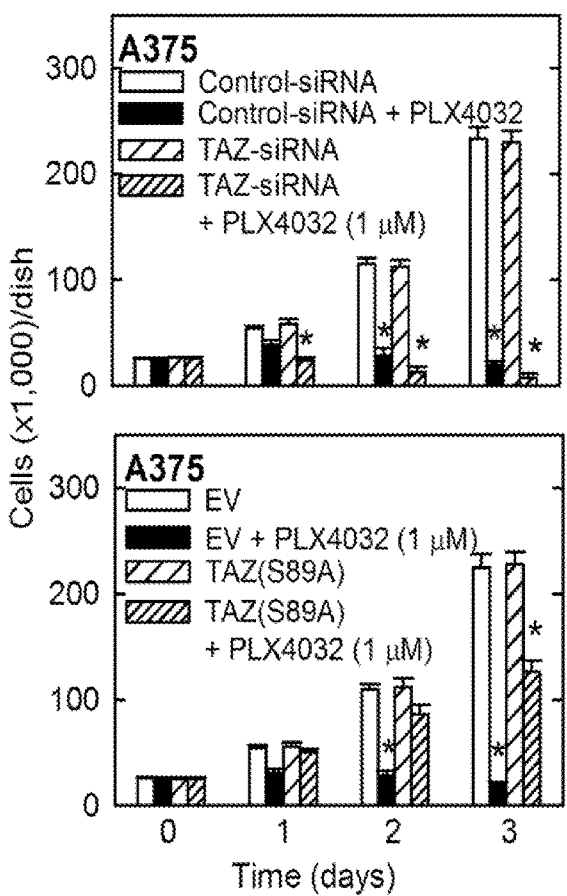
Figure 1I:
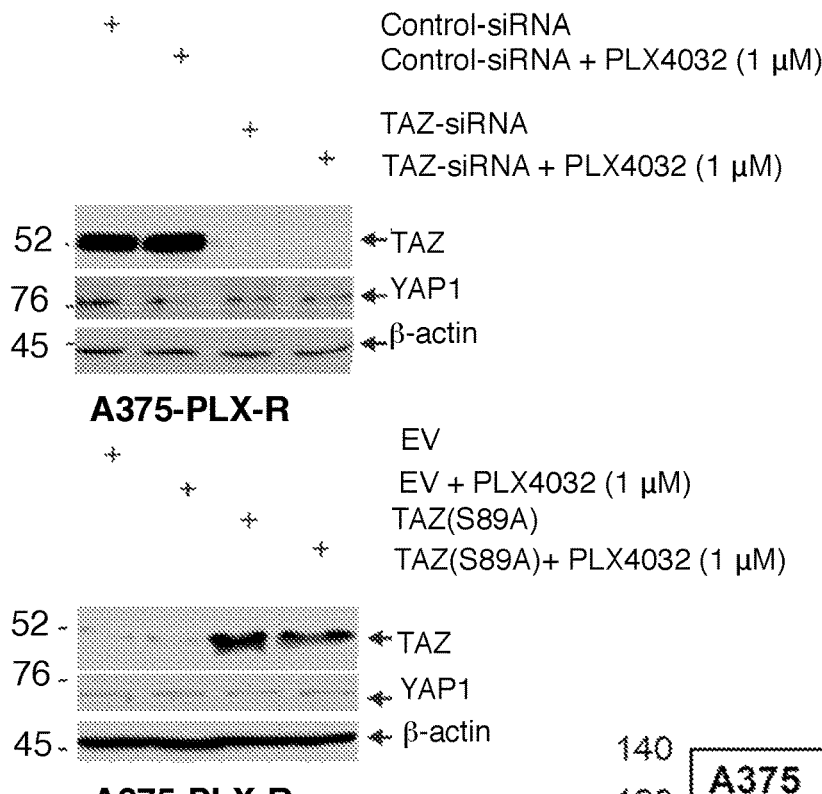

To confirm a biological role for these proteins, knockdown and overexpression experiments were performed. FIG. 1D shows that treatment with PLX4032 or YAP1-siRNA reduces A375 cell proliferation, and that expression of constitutively active YAP1, YAP(S127A), reversed the PLX4032-dependent growth suppression. Moreover, YAP1 knockdown reduced growth and restored A375-PLX-R cell response to PLX4032 (FIG. 1E). TAZ also influenced cell function. TAZ knockdown reduced A375 cell proliferation while TAZ overexpression partially reversed PLX4032-dependent growth suppression (FIG. 1F). TAZ knockdown also partially restored sensitivity of A375-PLX-R cells to PLX4032 (FIG. 1G). FIGS. 1G and 1I confirm the successful knockdown and overexpression of YAP1 and TAZ. These studies confirm previous studies (12,13,25) showing that YAP1 and TAZ are PLX4032 resistance factors.

EXAMPLE 3

Role of YAP1 and TAZ in MCS Cells

Figure 2A:
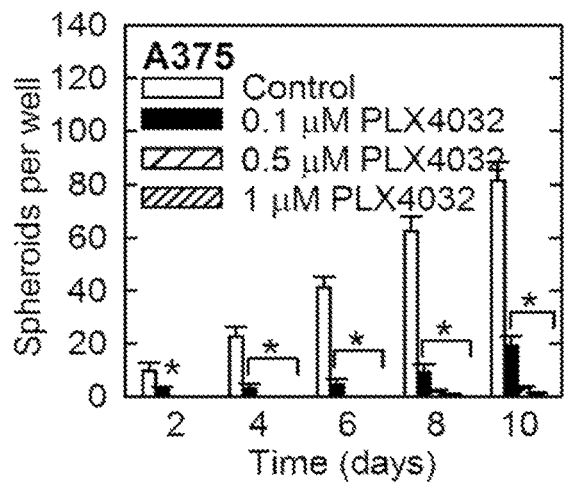
FIGS. 2A-2G shows the effect of BRAF inhibitor, PLX4032 on cell spheroid formation and invasion in A375 and A375-PLX-R cells.
Figure 2A:
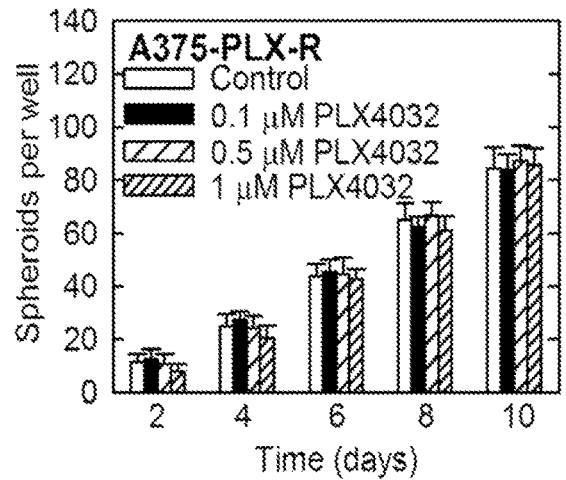
Figure 2B:
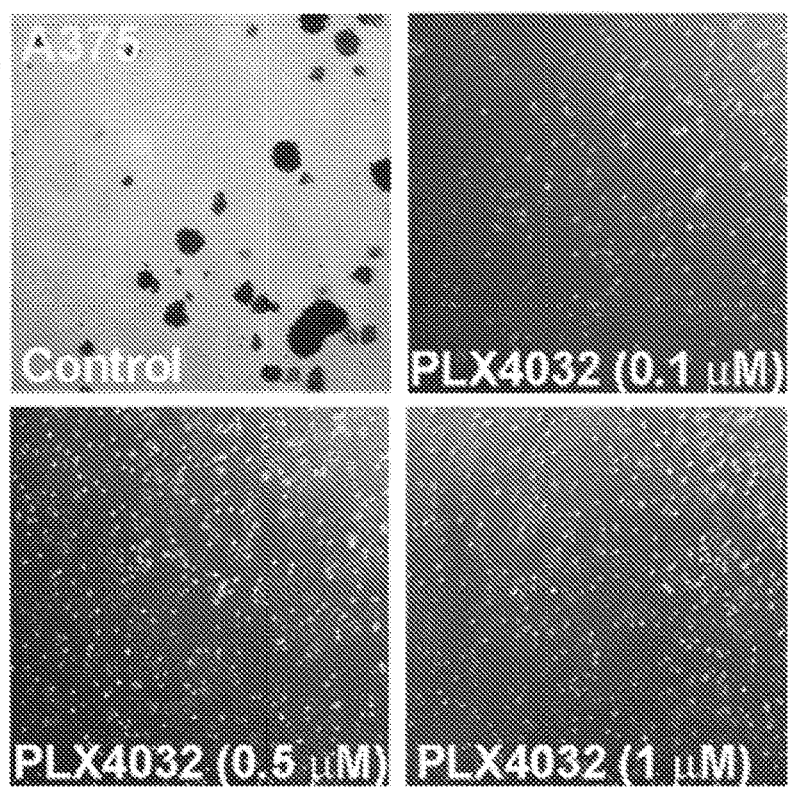
Figure 2B:
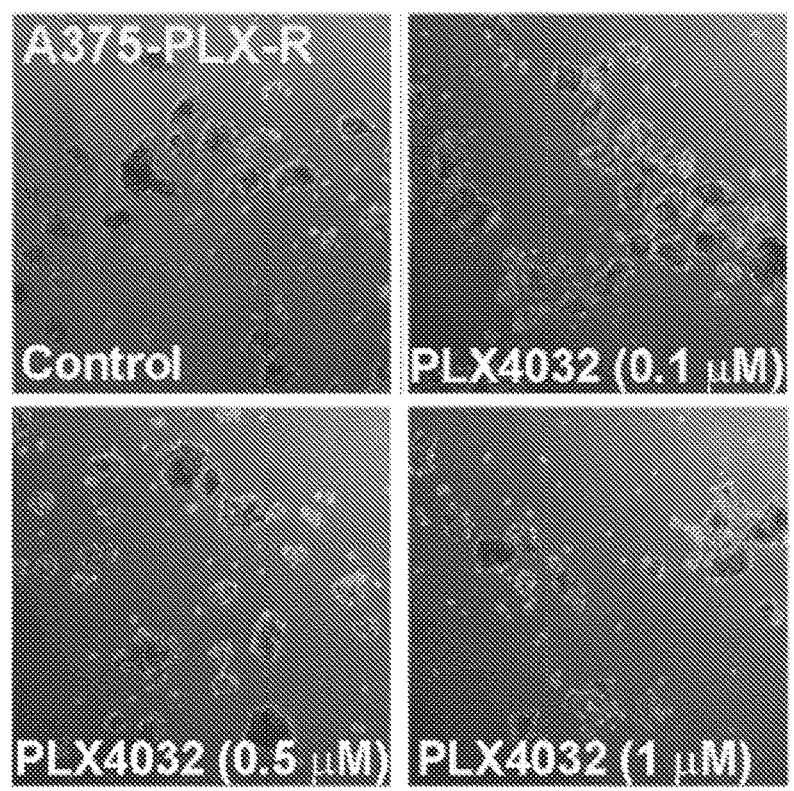
Figure 2C:
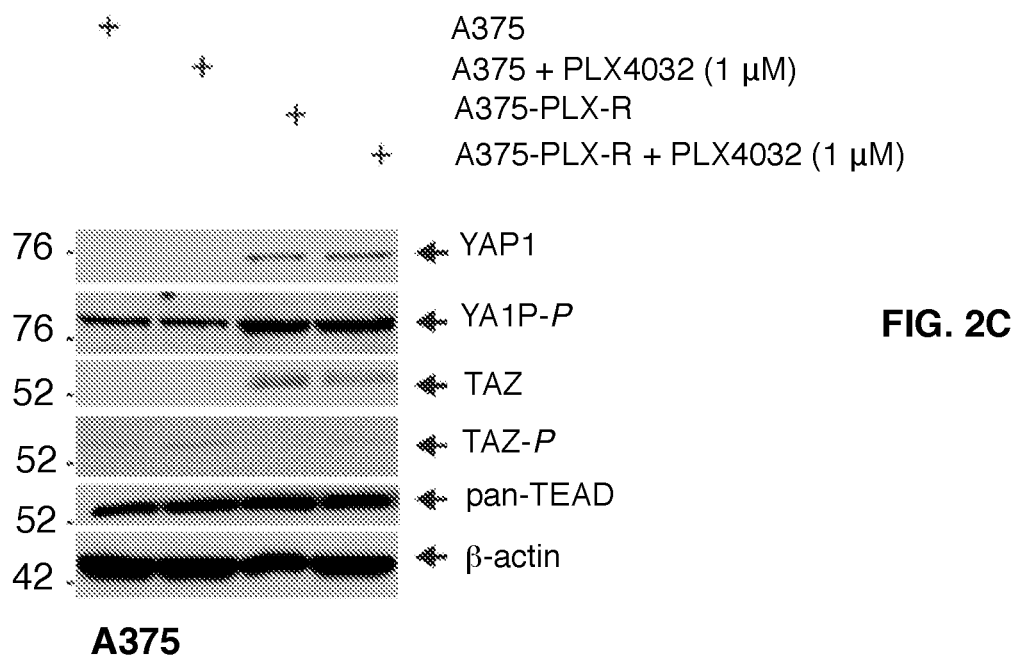
Figure 2D:
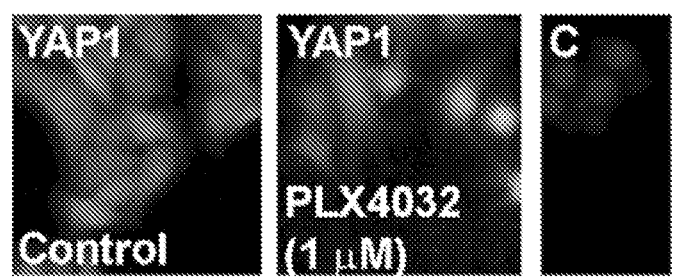
Figure 2D:
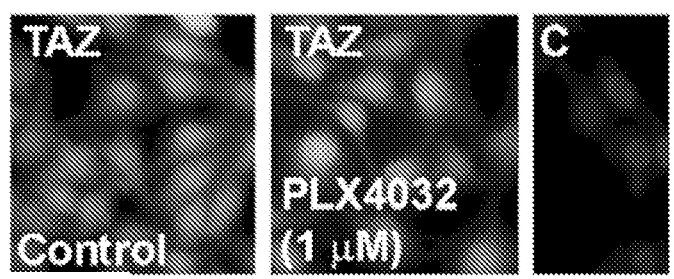

MCS cells can be selected by growth as spheroids and form rapidly growing, invasive and highly aggressive tumors as compared to non-stem melanoma cancer cells (26). The impact of PLX4032 treatment on MCS cell spheroids was examined. FIGS. 2A-2B shows that PLX4032 treatment suppressed A375 cell, but not A375-PLX-R cell, spheroid formation. FIG. 2C shows that A375-PLX-R cell-derived MCS cells expressed elevated YAP1, TAZ and TEAD levels as compared to A375 cell derived MCS cells. In addition, YAP1-P formation was increased, and TAZ-P formation reduced. These results are generally consistent with observations in monolayer culture (FIGS. 1A-1I). Subcellular distribution is reported to influence YAP1 and TAZ activity in some cell types and so it was determined if PLX4032 treatment influences YAP1/TAZ subcellular distribution. As shown in FIG. 2D, there was no major change in YAP1 intracellular distribution in control versus PLX4032-treated A375 cells, suggesting that altered YAP1/TAZ subcellular distribution does not explain the response to PLX4032 (FIG. 2D).

Figure 2E:
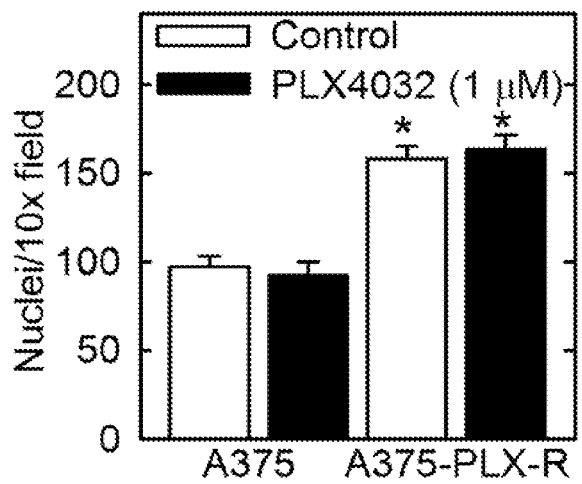
Figure 2F:
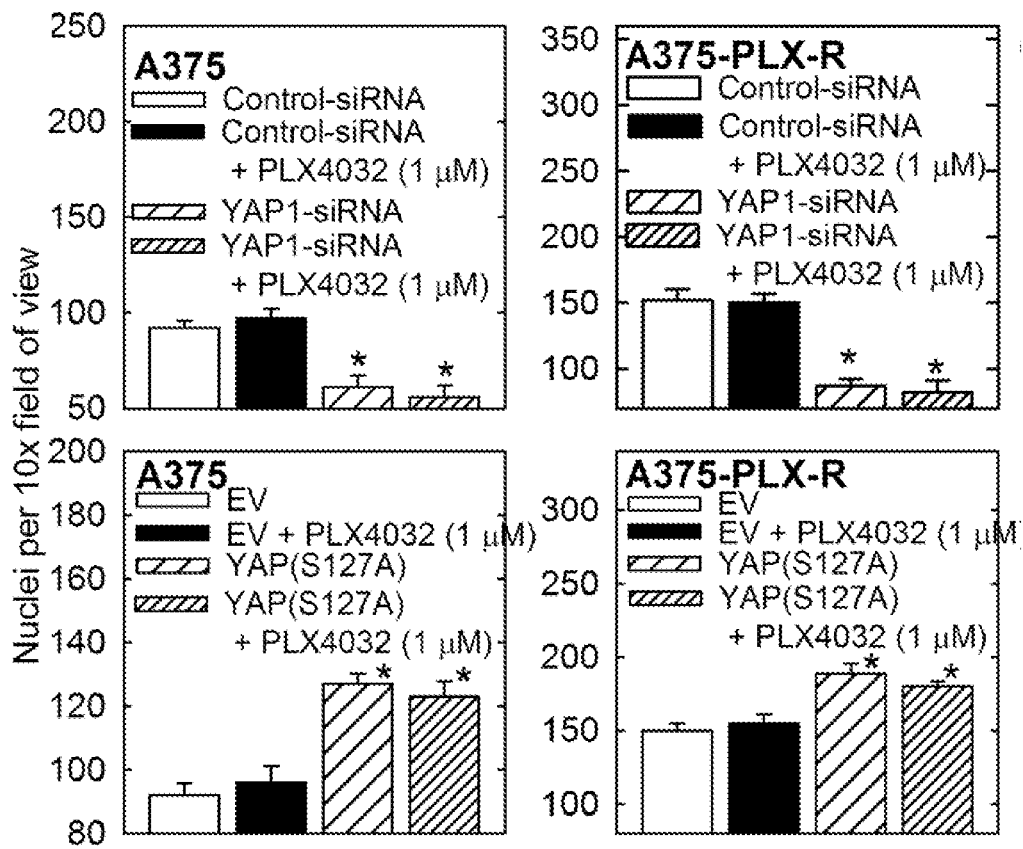
Figure 2G:
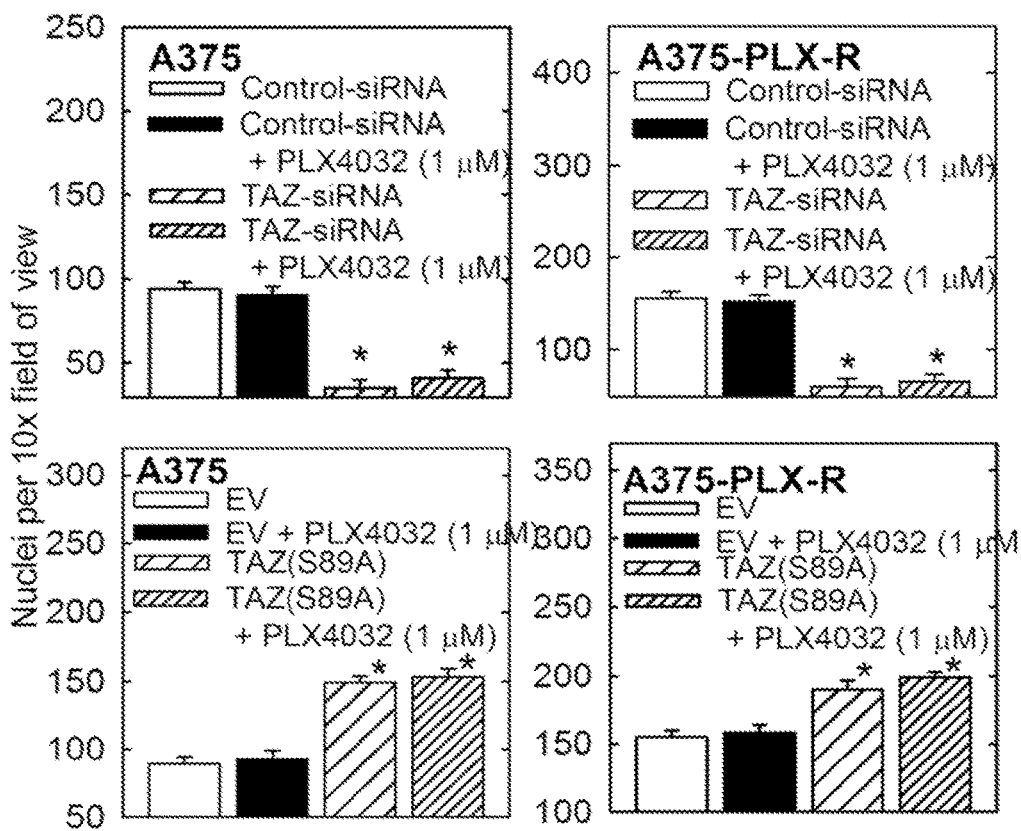

The PLX4032 impact on A375 and A375-PLX-R cell invasiveness was measured using a matrigel invasion assay. MCS cells display enhanced invasion which is a measure of metastatic aggressiveness (26). FIG. 2E shows that A375-PLX-R cell invasion is enhanced by 50% compared to A375 cells, but that invasion is not suppressed by PLX4032 in either cell type. FIGS. 2F-2G shows that although YAP1 or TAZ knockdown reduces invasion, PLX4032 treatment has no impact. These findings indicate that YAP1/TAZ knockdown does not sensitize the cells to PLX4032 with respect to matrigel invasion.

Figure 3A:
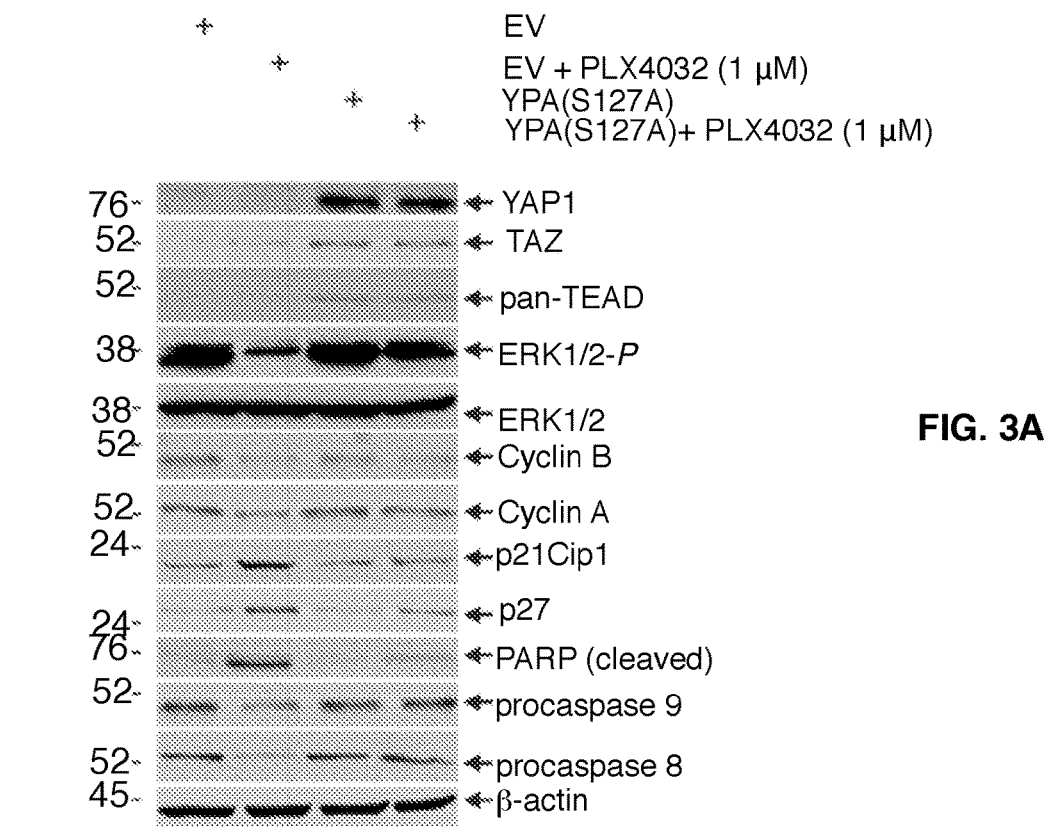
FIGS. 3A-3F show that YAP1 and TAZ prevent PLX4032-induced apoptosis.
Figure 3B:
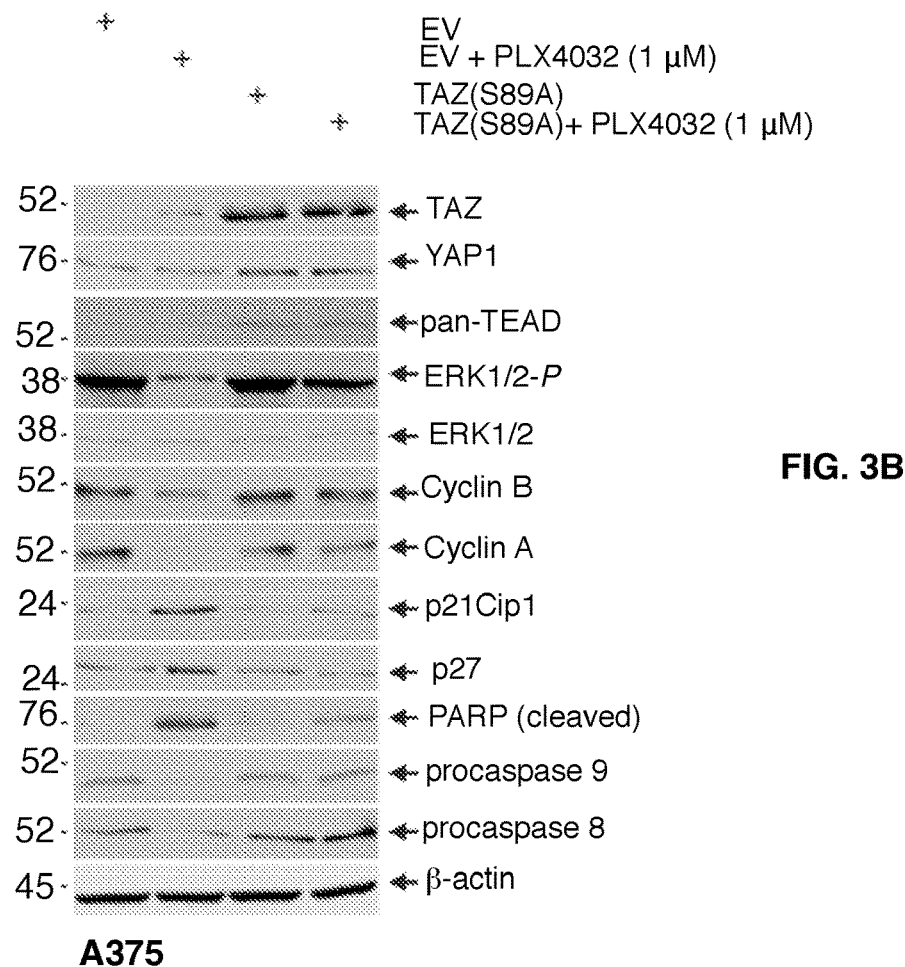

The above findings show that YAP1 and TAZ antagonize PLX4032 suppression of proliferation and spheroid formation. To understand the molecular mechanism of this antagonism, signaling changes were monitored in A375 cells following expression of YAP(S127A) and TAZ(S89A) and challenge with PLX4032. YAP(S127A) and TAZ(S89A) are constitutively actives forms of these proteins. Consistent with previous reports, BRAF inhibitors treatment reduces A375 cell ERK1/2 activity (FIGS. 3A-3B). Moreover, this is associated with reduced cyclin B and cyclin A, and increased p21$^{Cip1}$ and p27 (FIGS. 3A-3B). PLX4032 treatment also enhances apoptosis as measured by increased accumulation of cleaved PARP and reduced levels of procaspase 8 and 9. Consistent with a role for YAP1/TAZ in attenuating PLX4032 action, these changes are reversed by expression of constitutively-active forms of YAP1 (FIG. 3A) or TAZ (FIG. 3B). These findings are consistent with a previous report suggesting that YAP1 and TAZ antagonize BRAF inhibitors action by suppressing apoptosis (12). In addition, ERK1/2 signaling is suppressed in response to PLX4032 in A375 cells, but YAP(S127A) or TAZ(S89A) expression restored and maintained ERK1/2 signaling that is not reduced by PLX4032 treatment (FIGS. 3A-3B).

EXAMPLE 4

Role of TEAD Transcription Factors in MCS Cells

Figure 3C:
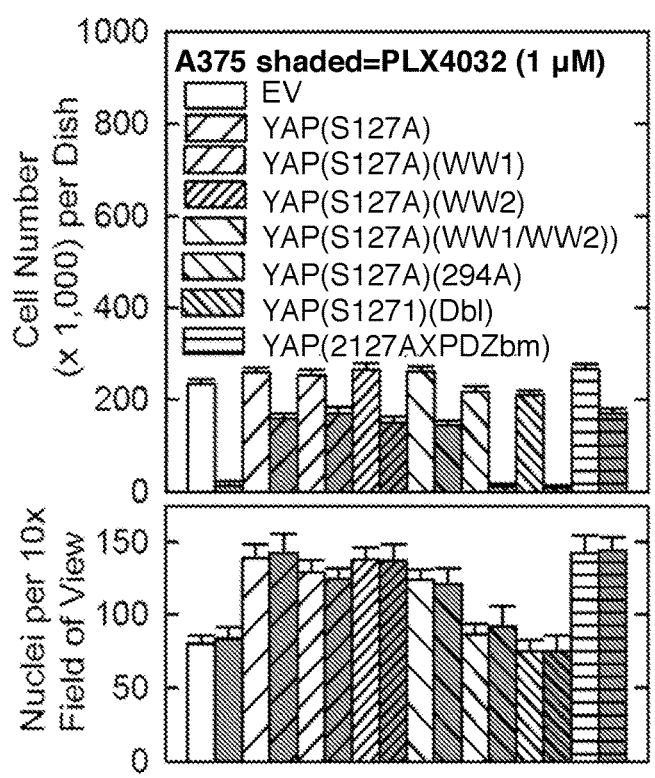

YAP1 interacts in the nucleus with TEAD transcription factors to regulate gene expression leading to enhanced cell proliferation and survival (6,16). Since YAP1 can also interact with other targets (27), it was determined whether YAP1/TEAD interaction is required for PLX4032 resistance. FIG. 3C shows that YAP(S127A) expression can reverse PLX4032 suppression of A375 cell proliferation. The ability of YAP(S127A) mutants, which cannot interact with selected cellular proteins, to replicate this response was monitored. YAP(S127A)(S94A) is a TEAD interaction domain mutant that is unable to interact with TEAD factors. YAP(S127A)(WW1), YAP(S127A)(WW2) and YAP (S127A)(WW1/WW2) has mutations in key tryptophan resides in the WW domains and cannot interact with WW domain binding proteins. YAP(S127A)(Dbl) is a double mutant combining the S94A and WW domain mutations, and YAP(S127A)(PDZbm) has a c-terminal 5 amino acid truncation that removes the PDZ binding domain (8). All of these constructs are able to restore cell proliferation in PLX4032-treated A375 cells, except for YAP(S127A) (S94A) and YAP(S127A)(Dbl). Both of these mutants encode the S94A mutation in the TEAD interaction domain which inactivates interaction with TEAD factors (FIG. 3C, upper panel). This indicates that YAP1 antagonism of PLX4032-dependent growth suppression requires YAP1 interaction with TEAD factors. The impact of each mutant and PLX4032 treatment on A375 cell matrigel invasion was measured. FIG. 3C (lower panel) tests the requirement for YAP1/TEAD interaction in this context. This data confirms, as shown in FIG. 2F, that YAP1 stimulates and PLX4032 does not regulate invasion. It also shows that all YAP (S127A) forms increase A375 cell matrigel invasion, except for the YAP(S127A)S94A and YAP(S127A)Dbl mutants that do not interact with TEAD factors.

Figure 3D:
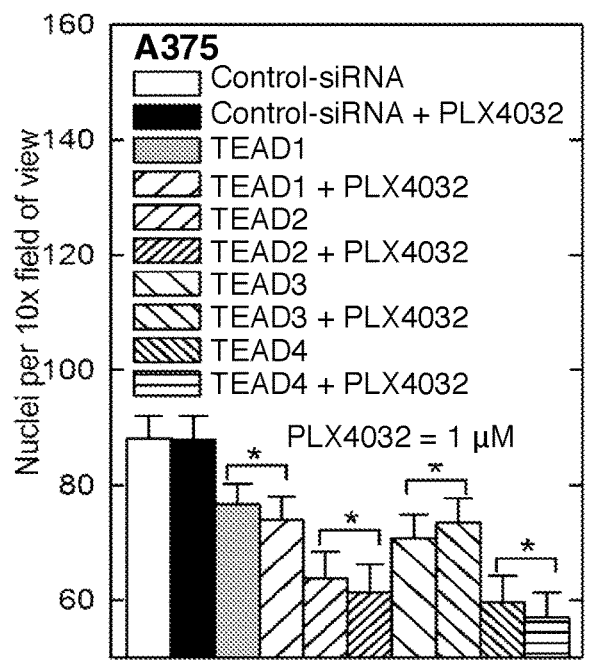
Figure 3D:
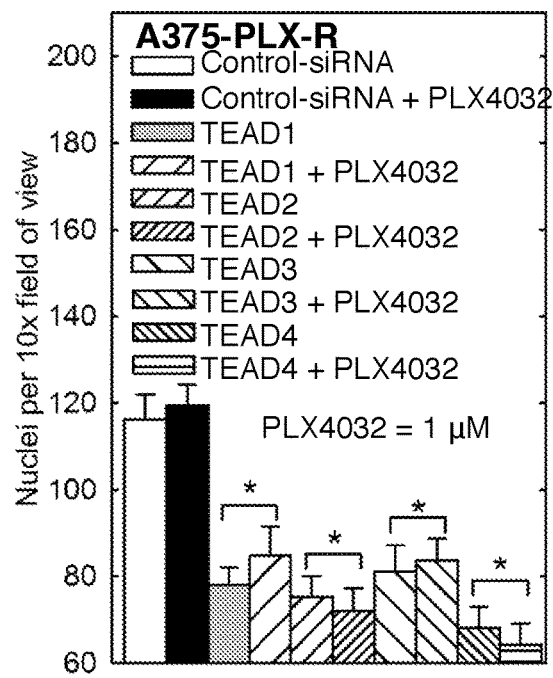
Figure 3D:
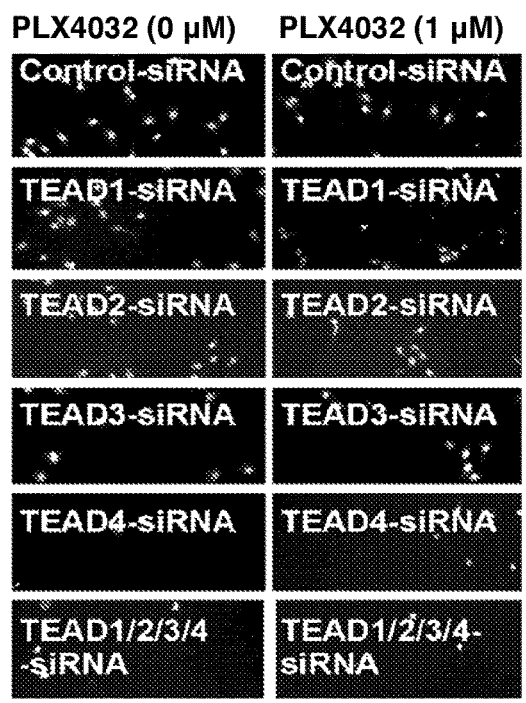
Figure 3E:
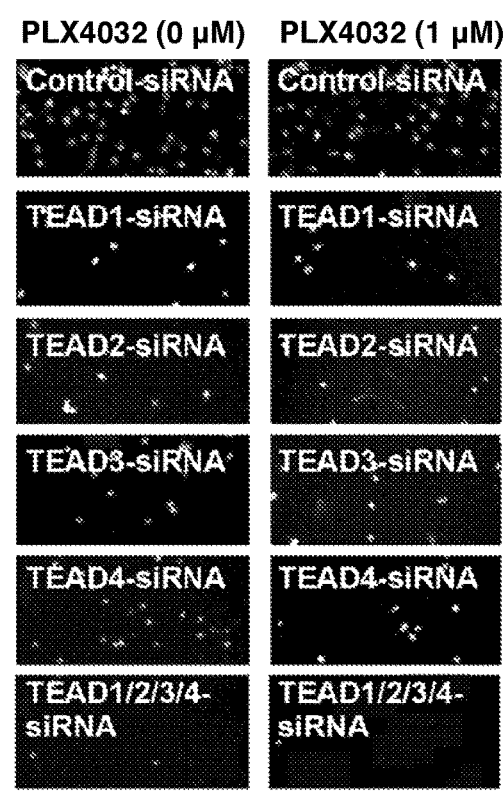
Figure 3F:
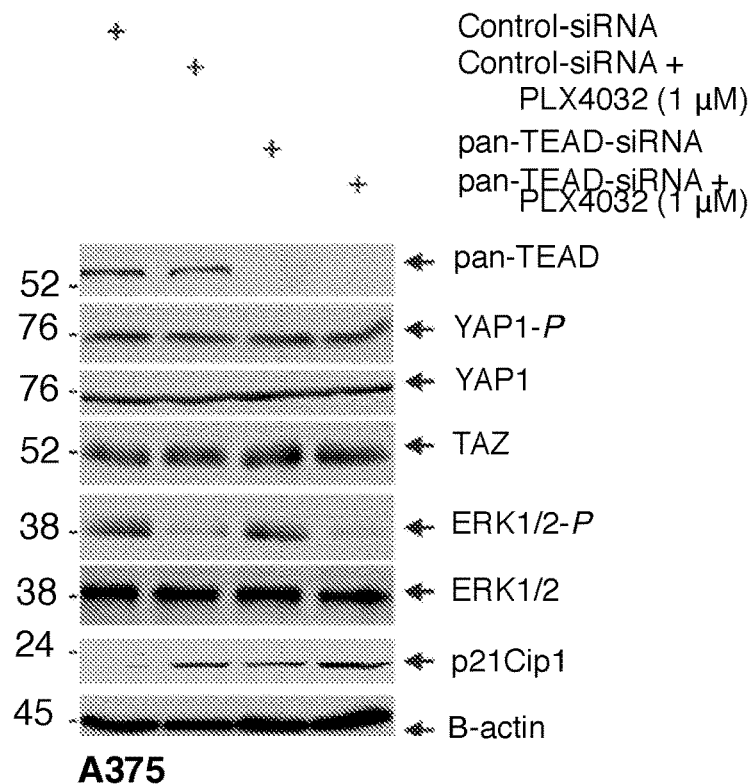
Figure 3F:
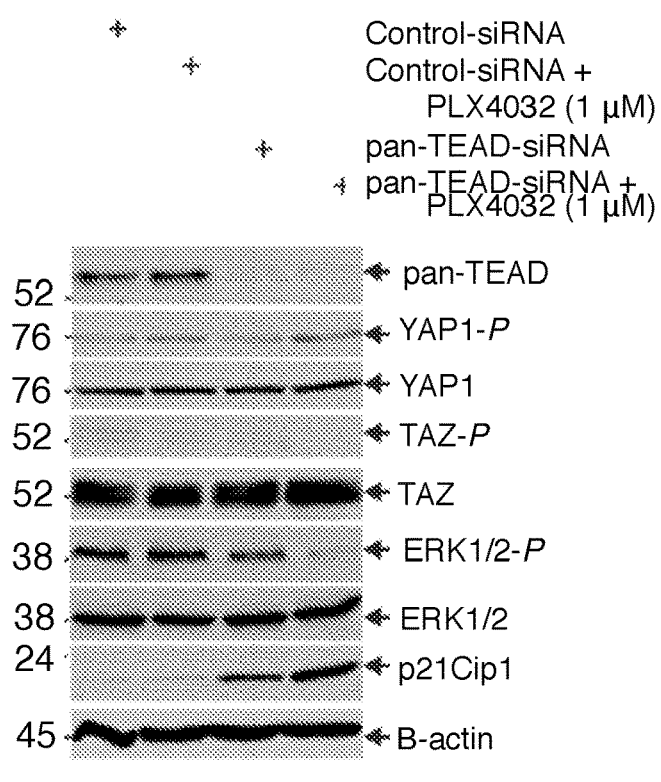

The impact of TEAD factor knockdown on invasion in PLX4032 sensitive and resistant cells was examined. PLX4032 resistant cells more efficiently invade matrigel as compared to PLX4032 sensitive cells (compare control group values in FIGS. 3D-3E). Moreover, loss of individual TEAD proteins reduces invasion, and simultaneous loss of all TEAD factors results in the greatest reduction (FIGS. 3D-3E). TEAD loss reduced PLX4032-resistant cell invasion (FIG. 3E) to the level observed in untreated PLX4032-sensitive A375 cells (FIG. 3D) but PLX4032 treatment did not impact invasion (FIGS. 3D-3E). We next examined the impact of PLX4032 on signaling in TEAD intact and knockdown A375 and A375-PLX-R cells. ERK1/2 phosphorylation is particularly interesting in that it is reduced in PLX4032-treated A375 cells in the presence or absence of TEADs. In contrast, ERK1/2 activity is only reduced in A375-PLX-R cells following TEAD knockdown and PLX4032 treatment (FIG. 3F). In contrast, TEAD knockdown does not appreciably alter YAP1, YAP1-P, TAZ or TAZ-P levels in either cell line, and p21$^{Cip1}$ levels are increased by PLX4032 treatment or TEAD knockdown (FIG. 3F).

EXAMPLE 5

Pharmacologic Inhibition of YAP1 and BRAF(V600E) on MCS Cell Survival

Figure 4A:
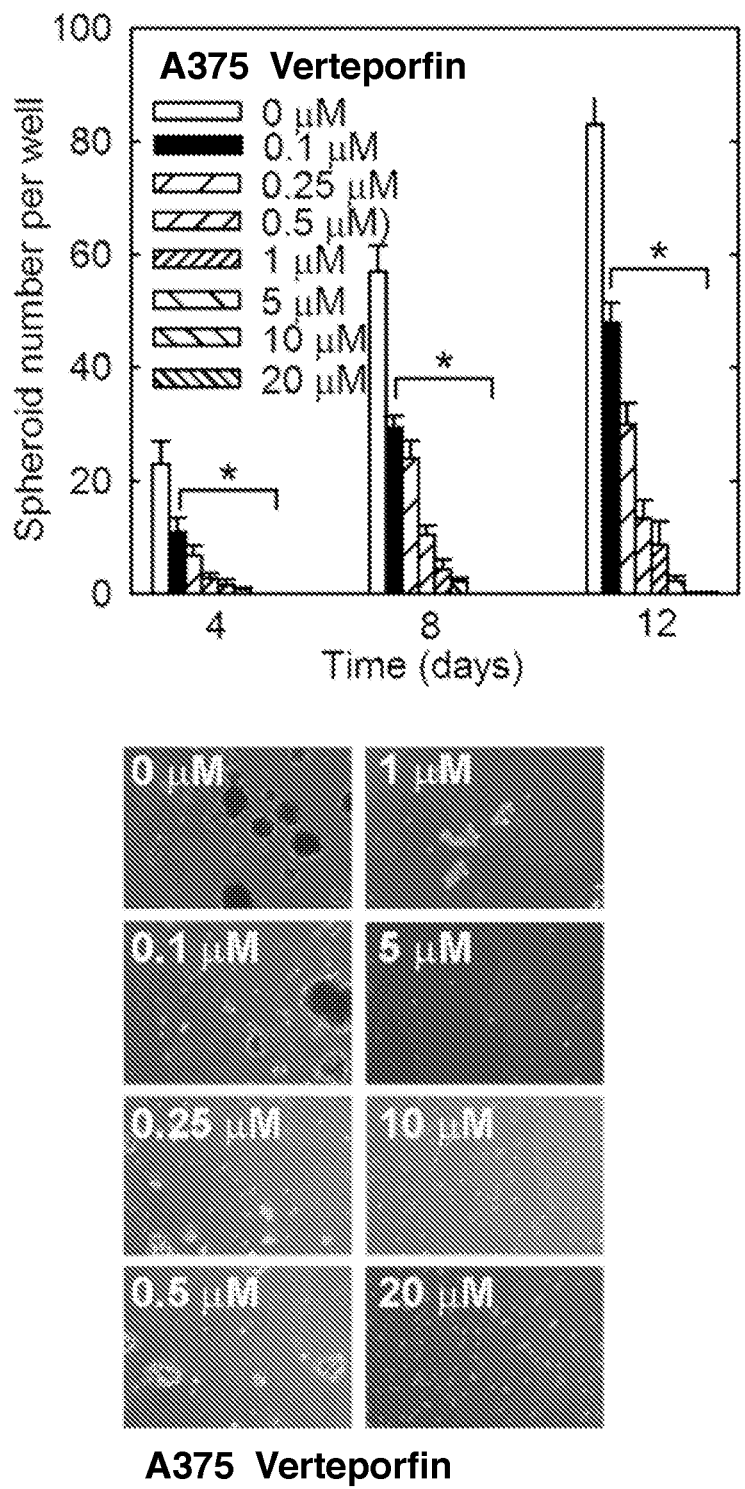
Figure 4B:
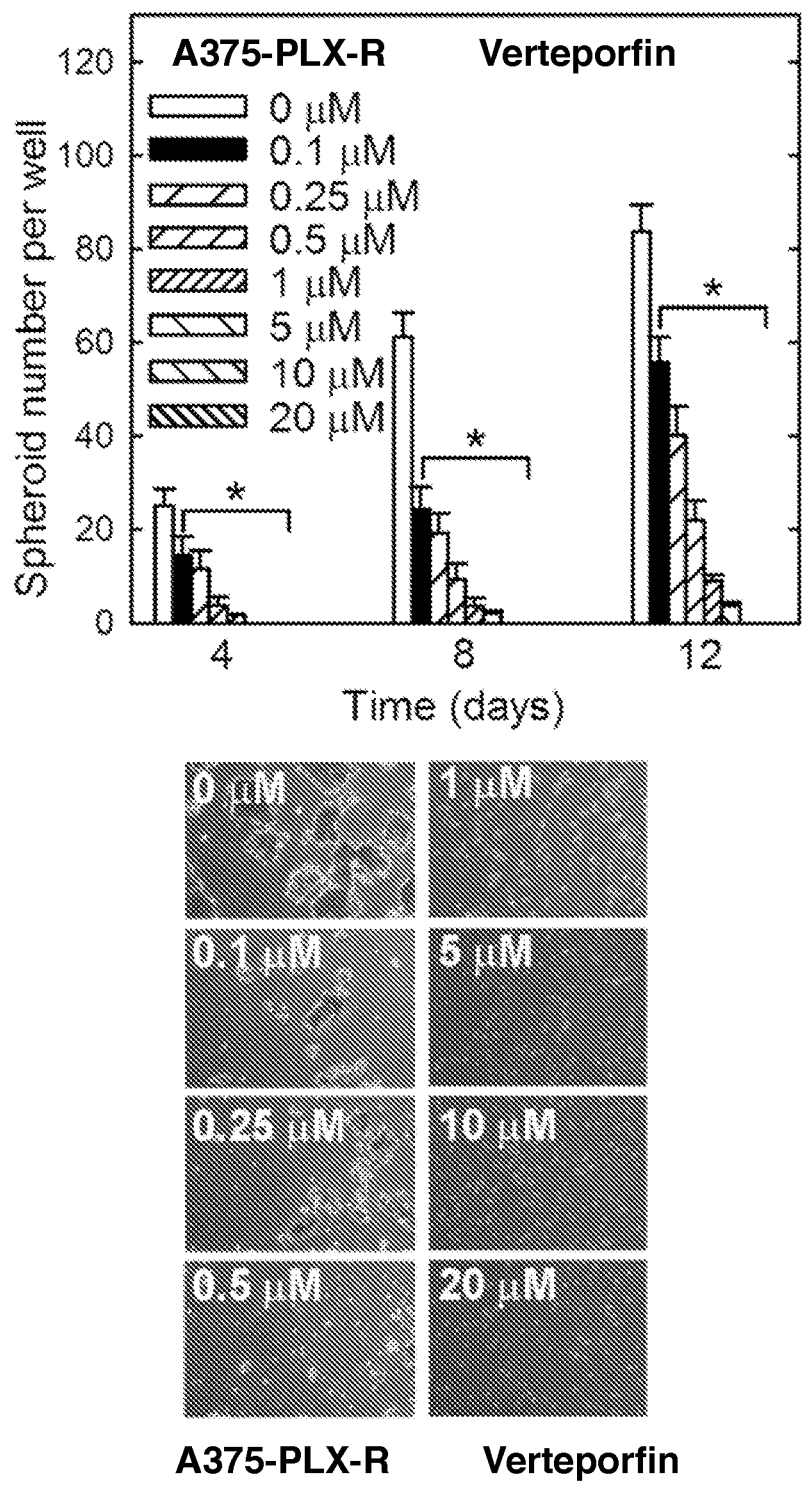
Figure 4C:
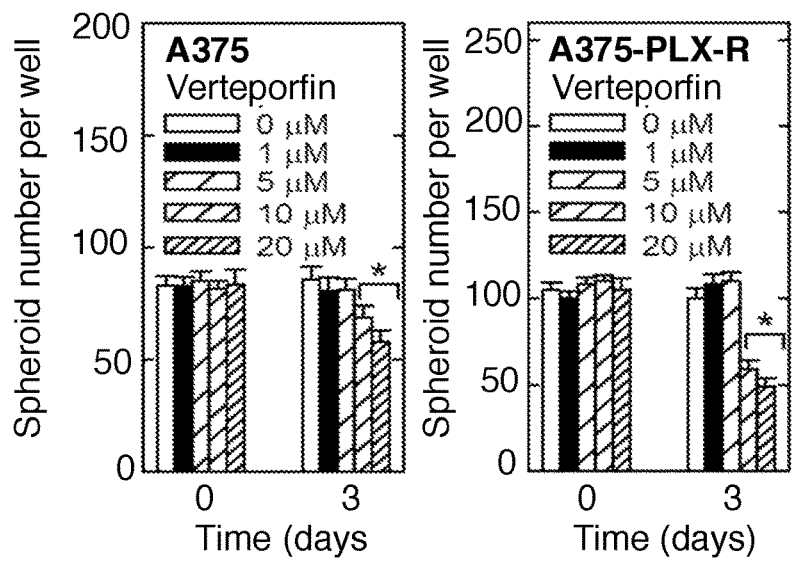
Figure 4D:
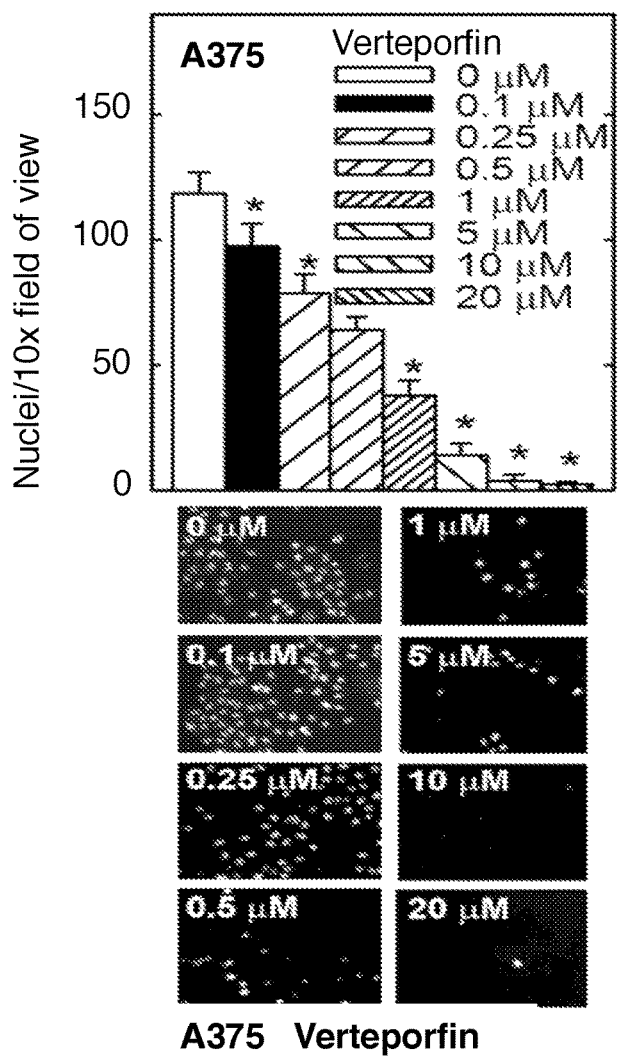

Identification of agents that suppress survival of PLX4032-resistant cells, or re-sensitize these cells to PLX4032, is an important goal. The experiments in FIG. 1D suggest that interfering with YAP1 function may achieve this objective. YAP1 interacts with TEAD transcription factors to drive gene expression (6,28) and a small molecular inhibitor called verteporfin has been reported to disrupt YAP1/TEAD interaction by binding to YAP1 and altering its structure (6,16). The impact of verteporfin treatment on spheroid formation and matrigel invasion in PLX4032 sensitive and resistant MCS cells was examined. FIGS. 4A-4B shows that verteporfin treatment suppresses A375 and A375-PLX-R spheroid formation by 50% at verteporfin concentrations as low at 0.1-0.25 mM and that spheroid formation is nearly completely inhibited at higher verteporfin concentrations. To demonstrate the effect of verteporfin on pre-formed spheroids, spheroids were permitted to form for 8 d and then treated with verteporfin. 20 mM verteporfin treatment reduced spheroid number/integrity (FIG. 4C) by 30-50% after a 3D treatment. Prolonged treatment results in complete destruction of the spheroids (not shown). FIGS. 4D-4E shows that matrigel invasion was 50% suppressed at concentrations of 0.5-1 mM verteporfin and that suppression was nearly complete at higher concentrations.

Figure 4G:
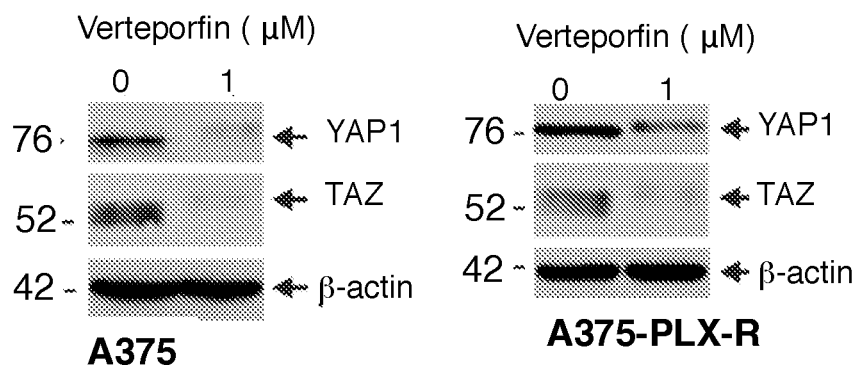
Figure 4H:
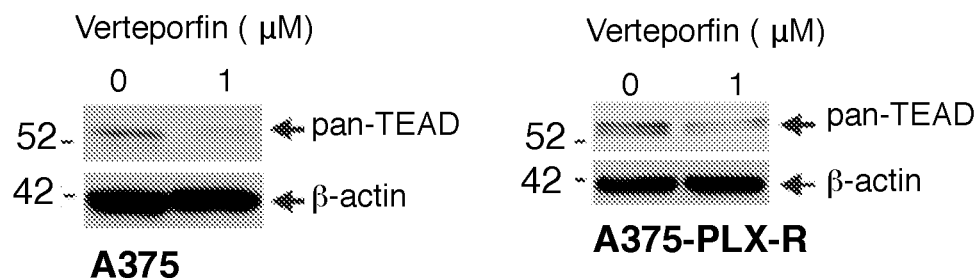
Figure 4I:
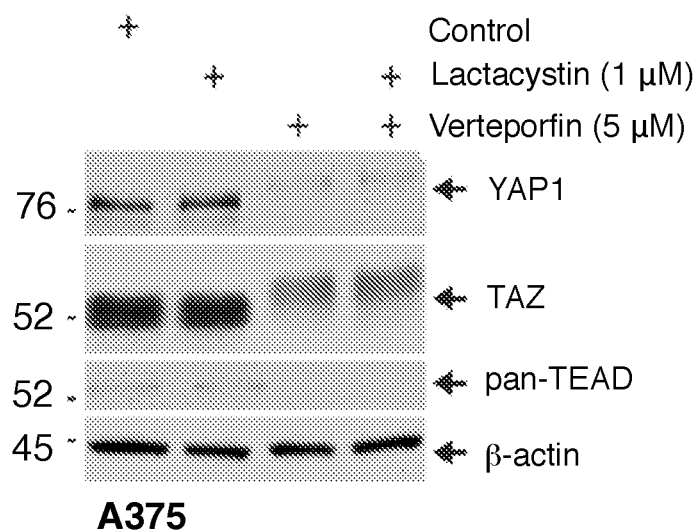

To understand the mechanism of verteporfin action, monolayer A375 and A375-PLX-R cells were treated with 1 mM verteporfin for 24 h and the impact on YAP1/TAZ mRNA and protein level was monitored. Verteporfin treatment did not impact the level of YAP1 or TAZ mRNA (FIG. 4F) but reduced YAP1 and TAZ protein levels (FIG. 4G). As shown in FIG. 4H, verteporfin treatment also reduced TEAD transcription factor levels. The proteasome is known to regulate YAP1/TAZ level (29,30) and so whether the proteasome was responsible for the observed reductions was examined. FIG. 4I shows the verteporfin-dependent reduction in YAP1, TAZ and TEAD level was not reversed by the proteasome inhibitor, lactacystin.

Figure 5A:
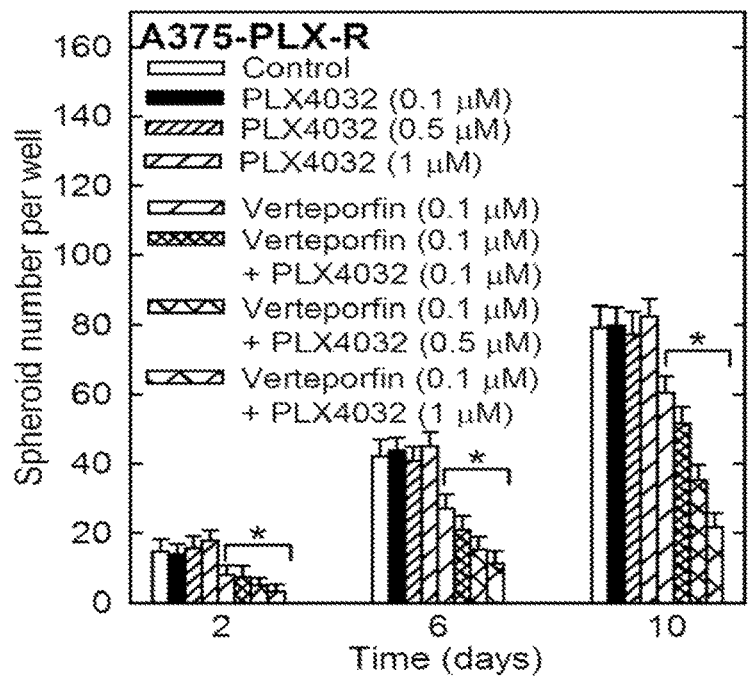
FIGS. 5A-5I show the effects of verteporfin on other PLX4032-resistant melanoma cancer cells.
Figure 5A:
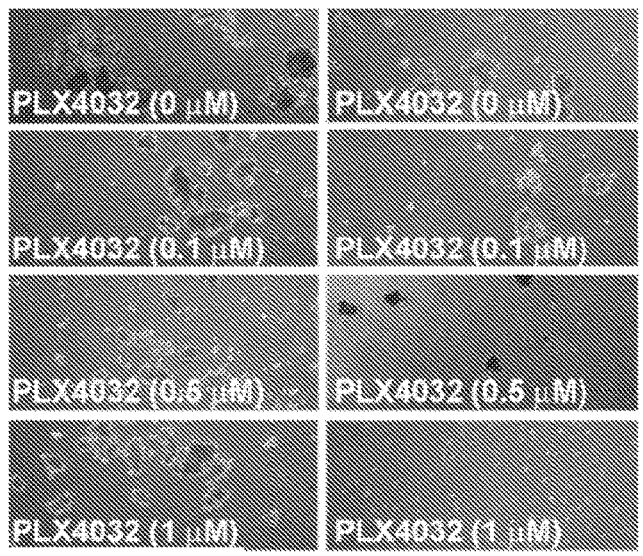

Whether verteporfin treatment restored PLX4032 sensitivity in resistant cells was examined. A375-PLX-R cells were plated in spheroid growth conditions and treated with 0-1 mM PLX4032 in the presence of 0 or 1 mM verteporfin and spheroid formation was monitored. FIG. 5A confirms that treatment with 0-1 mM PLX4032 did not suppress A375-PLX-R spheroid formation, but that co-treatment with 0.1 mM verteporfin restored PLX4032 suppression of spheroid number.

EXAMPLE 6

Verteporfin Suppresses Survival of Other PLX4032-Resistant Cell Lines

Figure 5B:
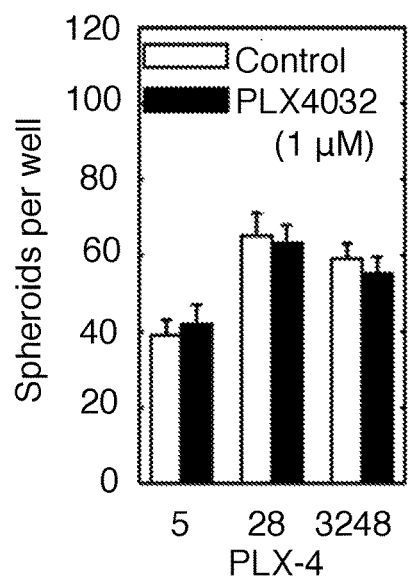
Figure 5C:
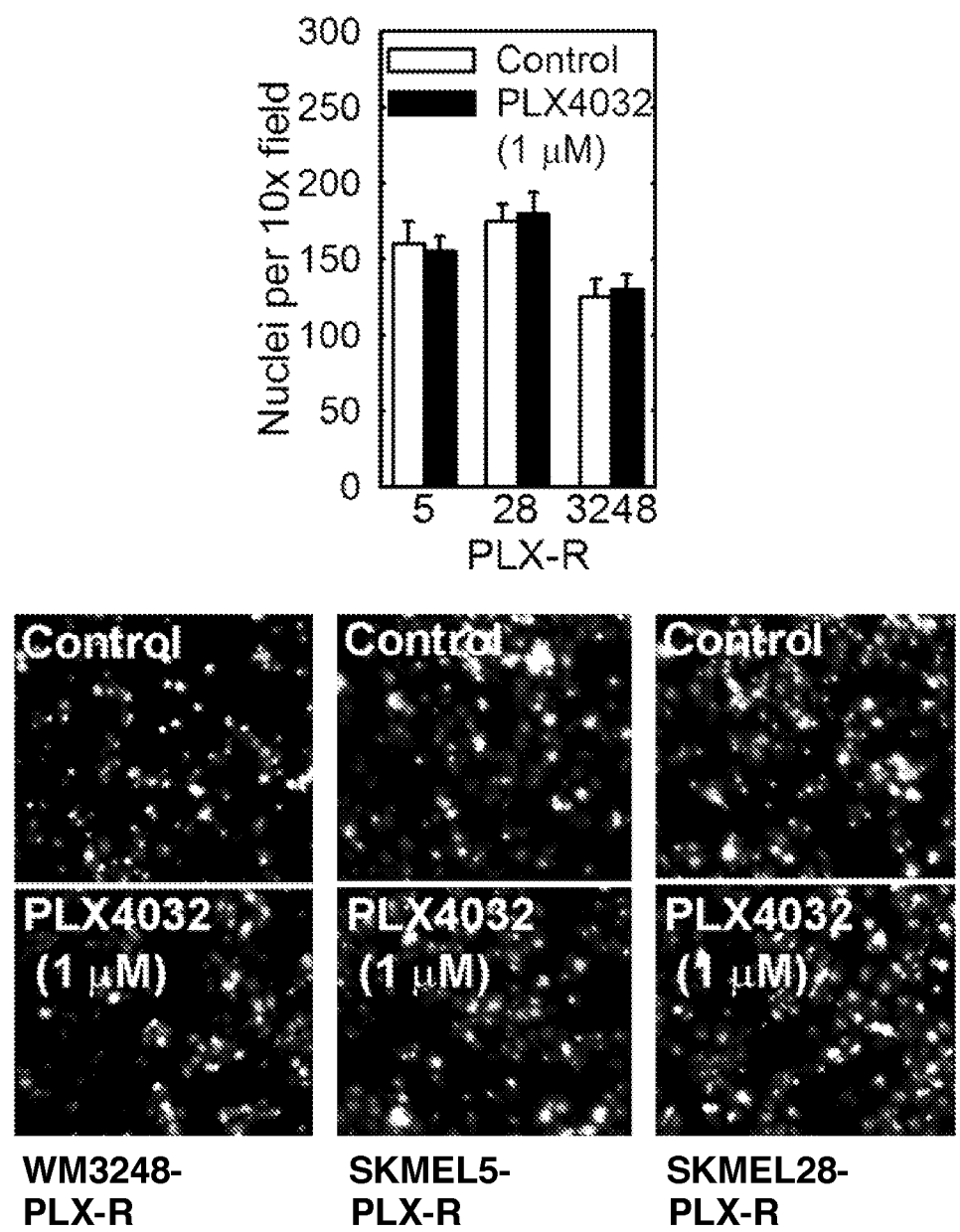
Figure 5D:
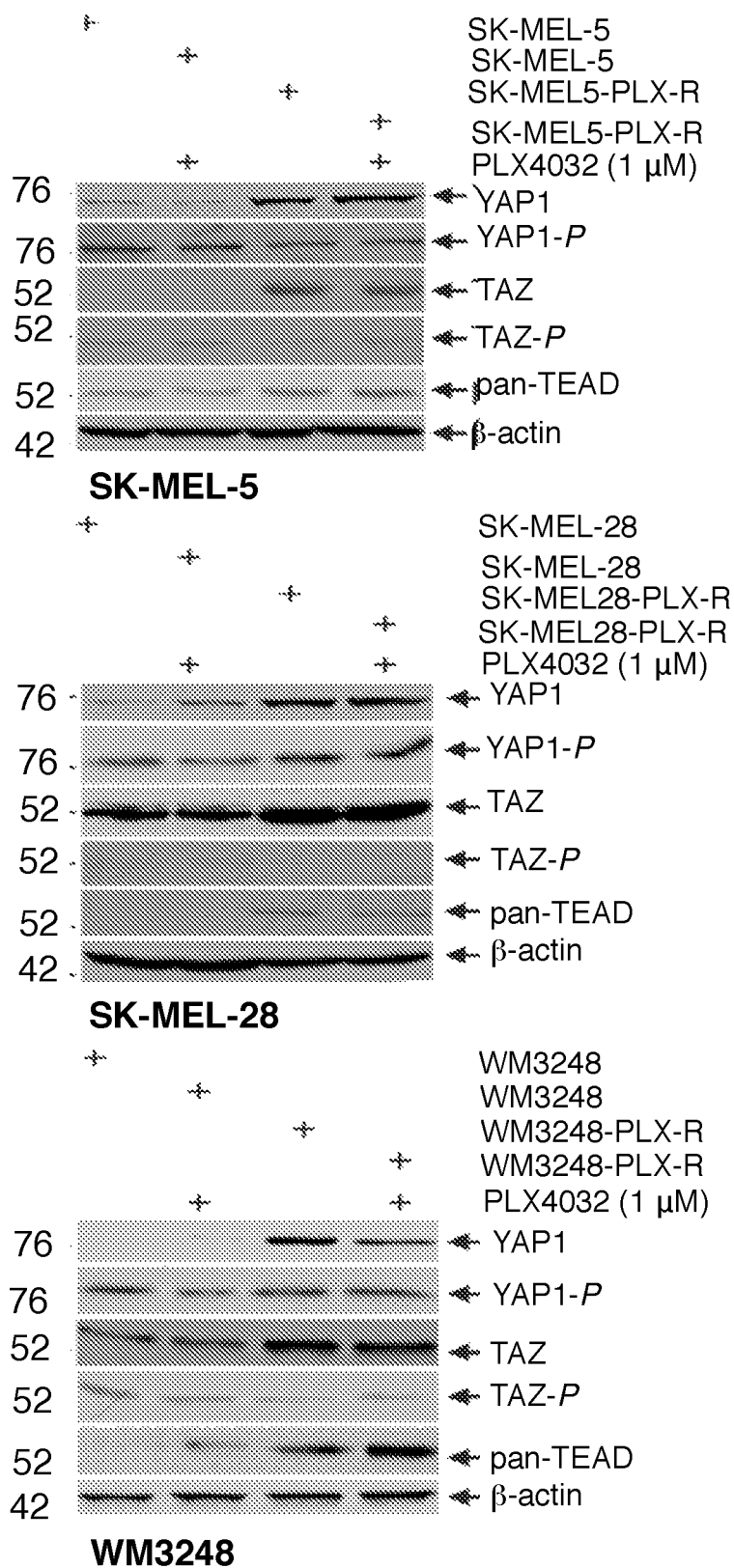
Figure 5E:
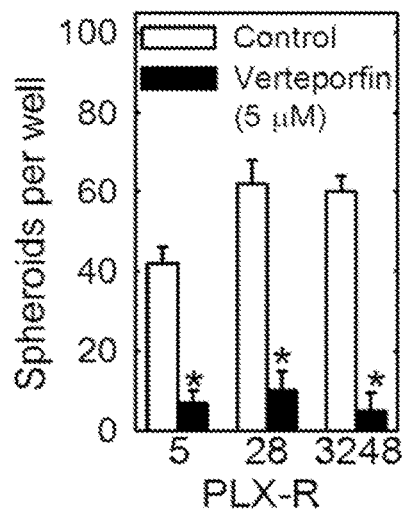
Figure 5F:
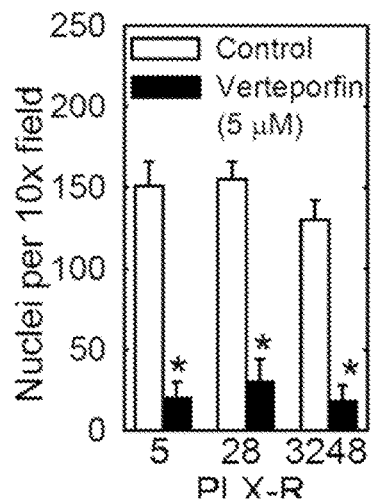
Figure 5F:
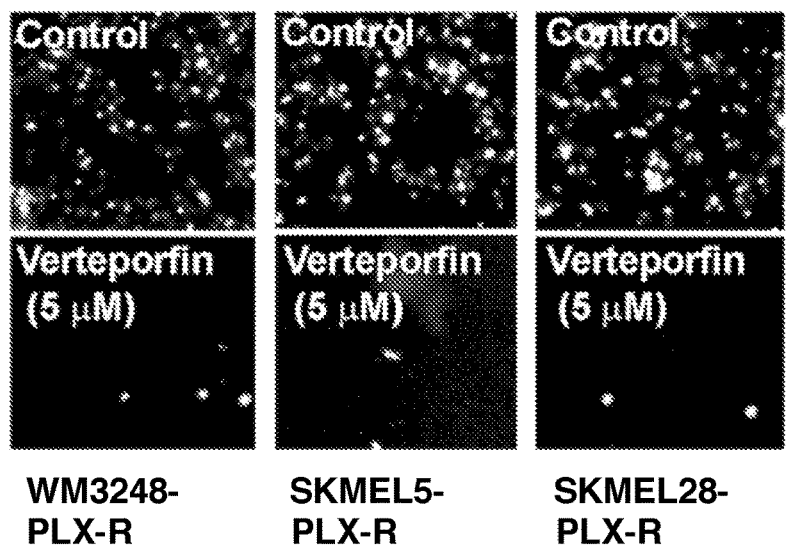
Figure 5G:
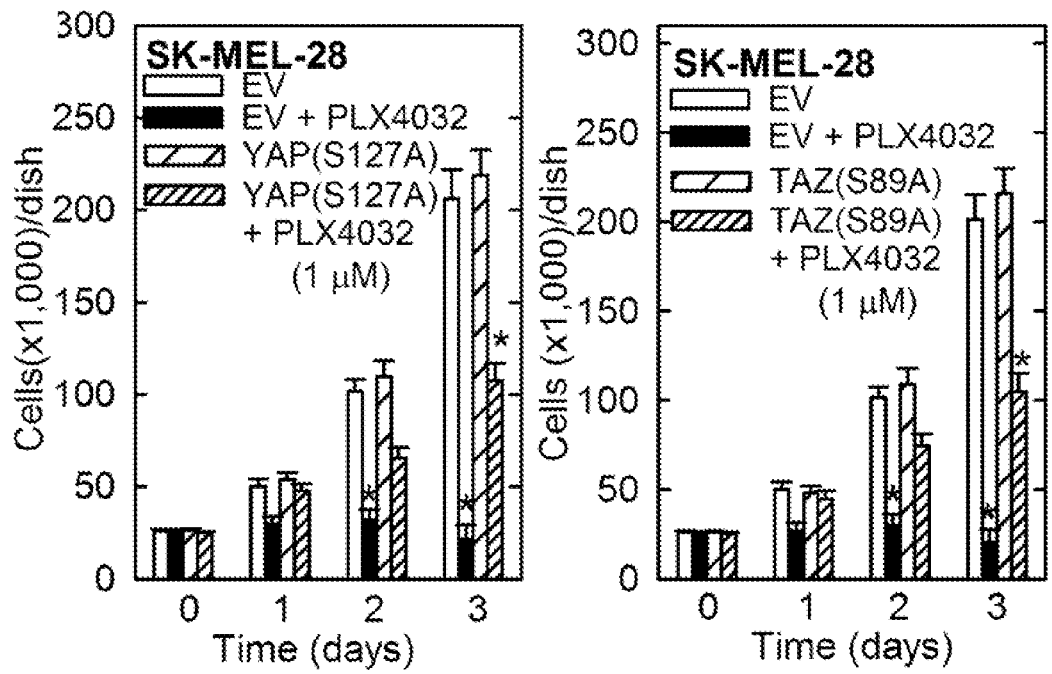

The impact of verteporfin on additional PLX4032 resistant melanoma cancer cell lines was examined. SK-MEL-5, SK-MEL-28 and WM3248 cells were selected for PLX4032 resistance by continuous growth in medium containing 1 mM PLX4032. FIGS. 5B-5C confirms that PLX4032 treatment did not reduce spheroid formation or matrigel invasion in these lines. Consistent with the findings in A375 and A375-PLX-R cells, YAP1, TAZ and TEAD levels were markedly increased in the resistant lines (FIG. 5D), a finding consistent with the hypothesis that these transcriptional regulators can contribute to PLX4032 resistance. FIGS. 5E-5F shows that verteporfin treatment reduced spheroid formation and matrigel invasion. To determine whether YAP1 and TAZ can antagonize PLX4032 action, constitutively active YAP1 and TAZ were expressed in wild-type SK-MEL-28 cells and the impact on cell proliferation was monitored. FIG. 5G shows that forced expression of YAP (S127A) or TAZ(S89A) partially reversed PLX4032 suppression of cell growth.

EXAMPLE 7

PLX4032 Resistant Cell Response to ERK Inhibitor

Figure 5H:
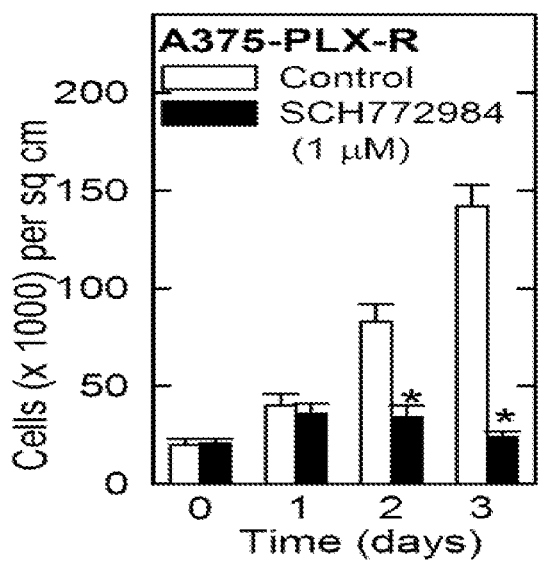
Figure 5I:
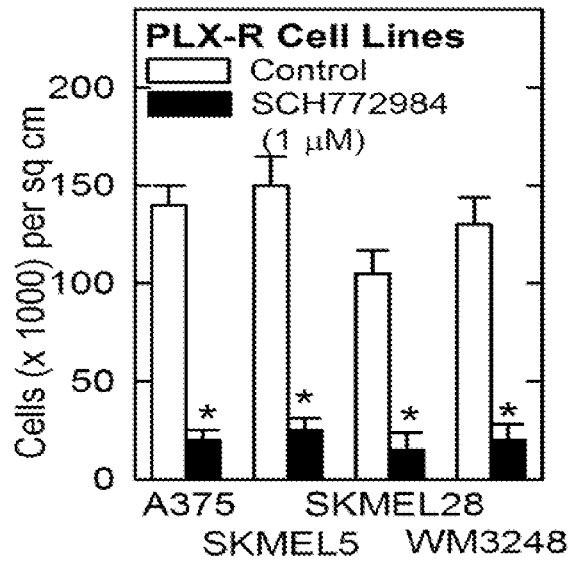

These findings suggest that YAP1/TAZ and TEADs foster melanoma cancer cell survival by maintaining ERK1/2 signaling as a mechanism to circumvent BRAF(V600E) inhibition (FIGS. 3A, 3B, 3F). This predicts that the BRAF inhibitors-resistant cells should remain sensitive to ERK1/2 inhibitors. To assess the role of ERK1/2 PLX4032 resistant cells were treated with SCH772984, a specific inhibitor of ERK1/2 (31), and the impact on cell proliferation was monitored. SCH772984 treatment produced a time-dependent reduction in A375-PLX-R cells number (FIG. 5H) and also reduced proliferation of SKMEL5-PLX-R, SKMEL28-PLX-R and WM3248-PLX-R cells (FIG. 5I).

EXAMPLE 8

Impact of Verteporfin and BRAF Inhibitors Co-Treatment on Tumor Formation

Figure 6A:
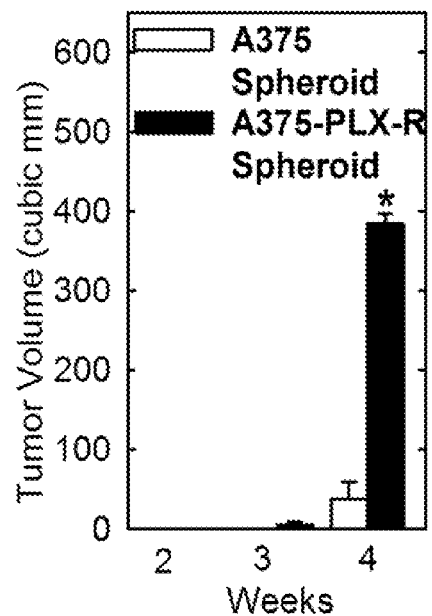
FIGS. 6A-6H show the effect of verteporfin on tumor formation.
Figure 6B:
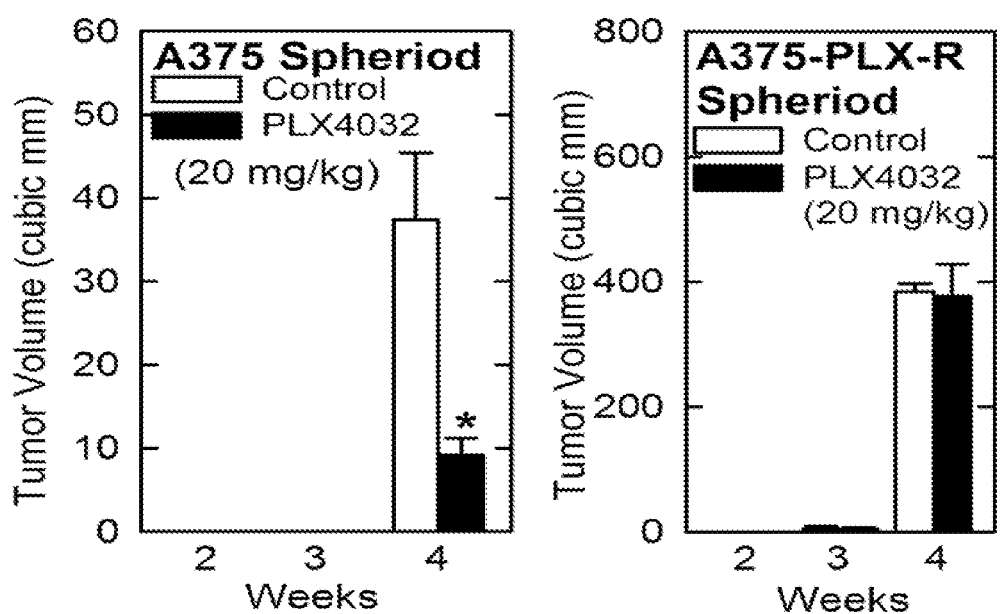
Figure 6C:
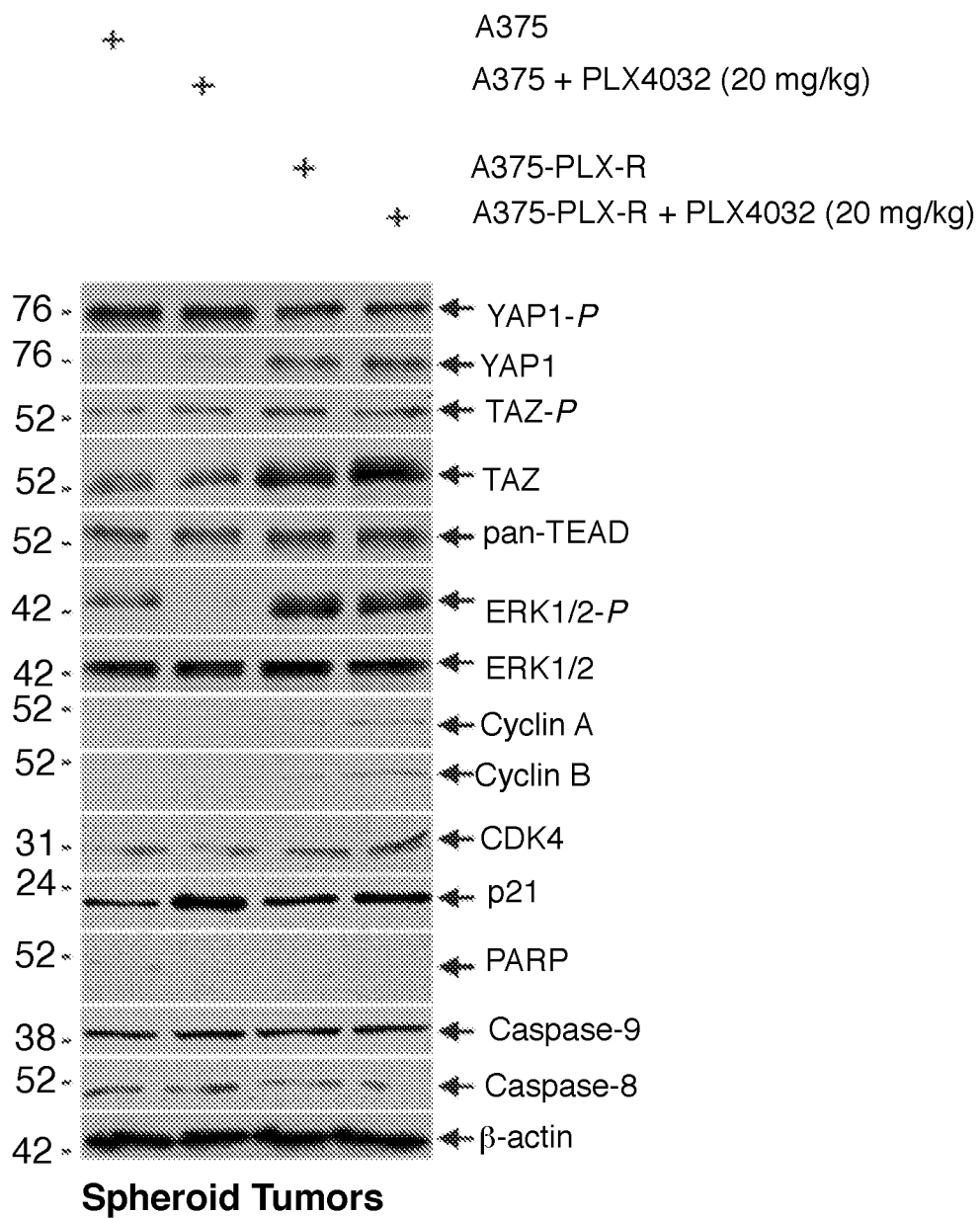
Figure 6D:
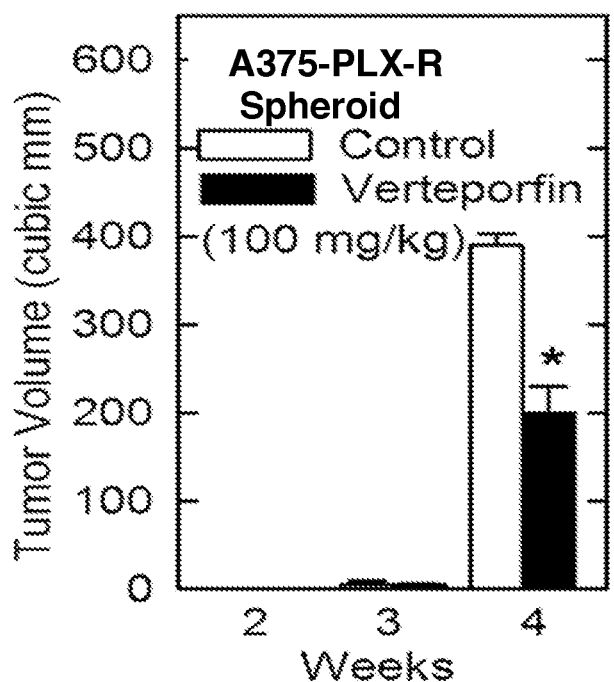
Figure 6E:
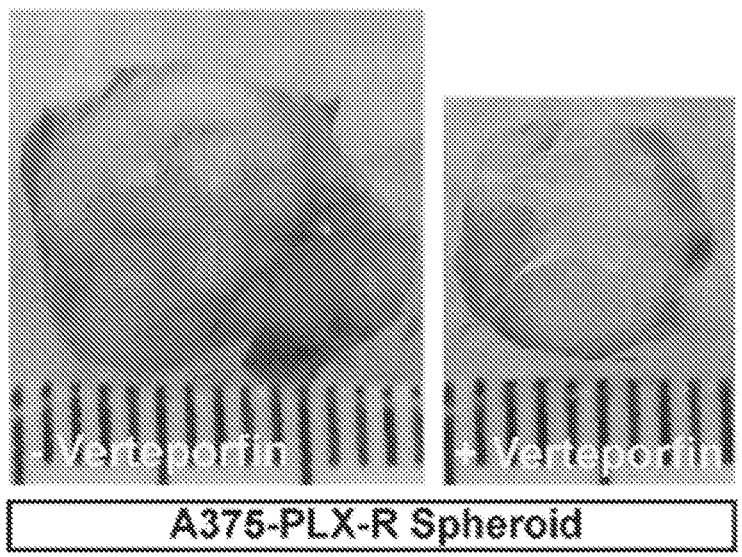
Figure 6F:
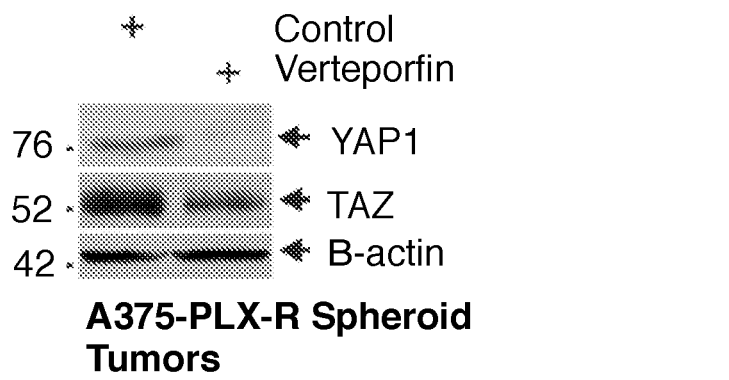

The impact of verteporfin on melanoma cell tumor formation was examined. MCS cells were selected as these cells display markedly enhanced malignant potential (26). A375-PLX-R derived MCS cells formed large tumors compared to A375 MCS cells (FIG. 6A), and PLX4032 suppressed growth of A375 but not A375-PLX-R spheroid cell-derived tumors (FIG. 6B). Moreover, consistent with the cell culture findings, the A375-PLX-R spheroid cell-derived tumors expressed elevated levels of YAP1, TAZ and TEADs as compared to A375 spheroid cell-derived tumors (FIG. 6C). In addition, ERK1/2-P, cyclins A and B, and CDK4 levels were elevated in A375-PLX-R spheroid cell-derived tumors (FIG. 6C). $p21^{Cip1}$ level was selectively slightly elevated in PLX4032-treated A375 spheroid cell-derived tumors (FIG. 6C), a finding that is consistent with their sensitivity to PLX4032 growth inhibition. The increase in YAP1, TAZ and TEADs in PLX4032 resistant tumor-derived MCS cells reflected the changes observed in cultured PLX4032-resistant cells, and indicated that elevated levels of YAP1, TAZ and TEAD factors were retained during growth in PLX4032 resistant tumors (FIG. 2C). The impact of inhibiting YAP1 function on tumor formation was assessed. FIGS. 6D-6F shows that verteporfin treatment suppressed YAP1 and TAZ level and that this is associated with reduced tumor size.

Figure 6G:
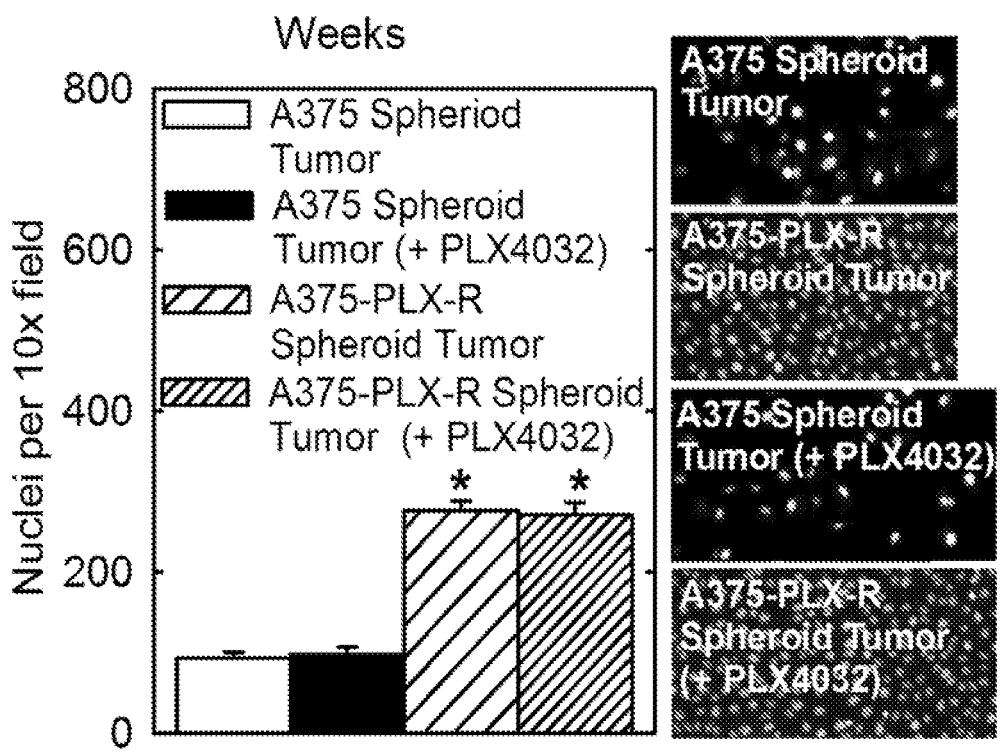
Figure 6H:
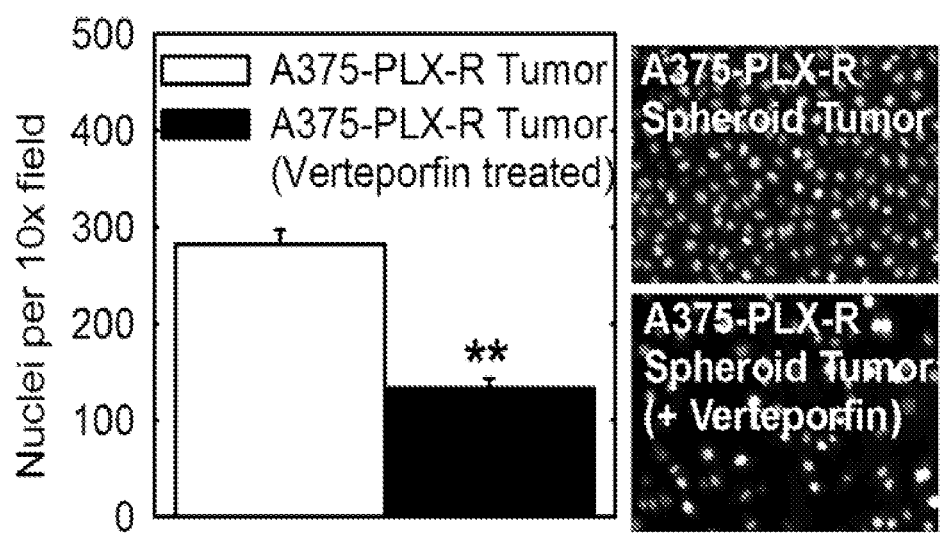

To measure whether verteporfin treatment influences the cancer stem cell status in the tumor, the tumor cells were harvested and the efficiency of matrigel invasion in the absence of drug treatment was examined. FIG. 6G shows that the tumor-derived A375-PLX-R cells invaded matrigel nearly three times as efficiently as tumor-derived A375 cells, and that in vivo PLX4032 treatment does not suppress matrigel invasion of sensitive or resistant cells (FIG. 6G). In contrast, verteporfin treatment of tumors reduced tumor formation and yielded a cell population with reduced matrigel invasion (FIG. 6H).

EXAMPLE 9

Verteporfin Treatment Restores Tumor Response to BRAF Inhibitors

Figure 7A:
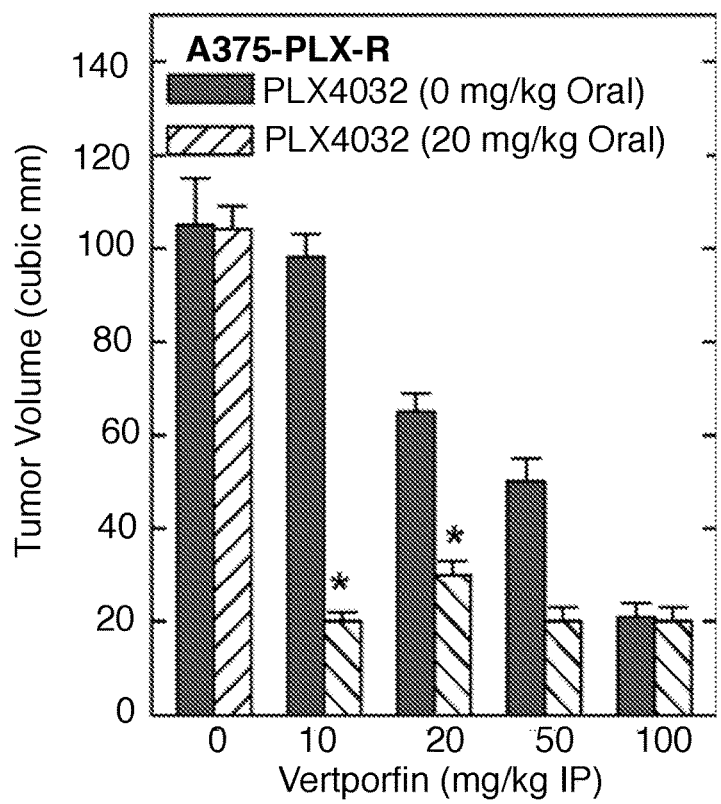
FIGS. 7A-7C shows that verteporfin restores PLX4032 suppression of ERK1/2 signaling and tumor formation.
Figure 7B:
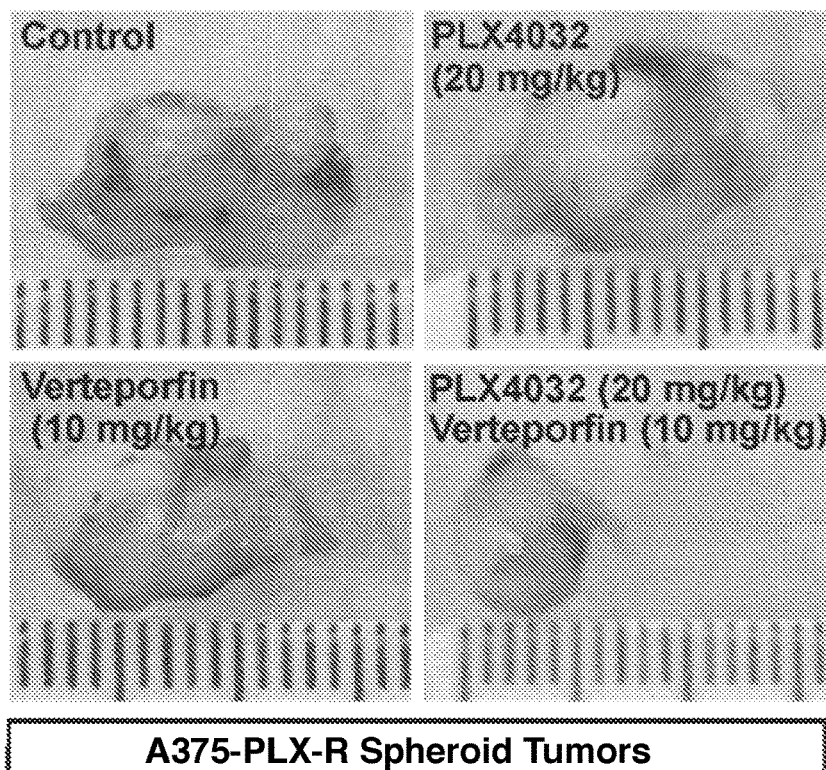
Figure 7C:
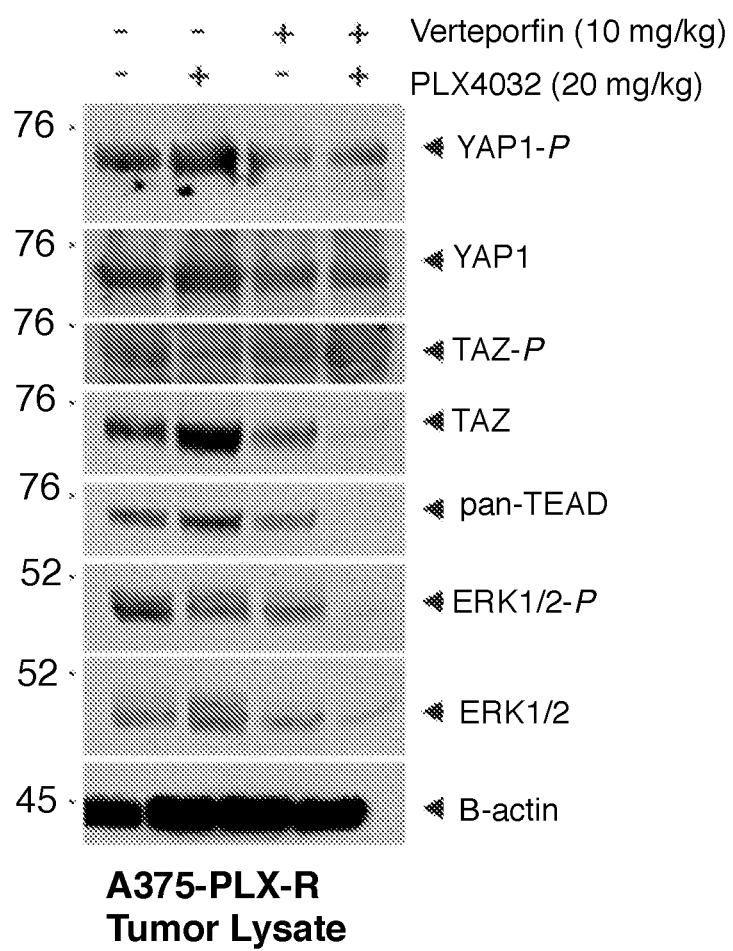

To demonstrate that inhibition of YAP1 function may restore PLX4032 suppression of tumor formation, the impact of treatment with 20 mg/kg PLX4032 was measured in the presence of 0-100 mg/kg verteporfin on tumor formation by spheroid-derived A375-PLX-R cells. FIGS. 7A-7B shows that in the absence of verteporfin, PLX4032 did not suppress A375-PLX-R tumor formation. However, verteporfin treatment produces a dose-dependent reduction in tumor size. The key observation is that treatment with a low concentration of verteporfin (10 mg/kg), that does not suppress tumor formation, restores PLX4032-dependent suppression of tumor formation. An examination of the biochemical status of the 10 mg/kg verteporfin/20 mg/kg PLX4032-treated tumors revealed a reduction in YAP1, YAP1-P, TAZ and TEAD levels (FIG. 7C). In addition, in the presence of verteporfin, PLX4032 treatment reduced ERK1/2-P level. These findings show that treatment with low levels of verteporfin, that do not impact tumor formation, can re-sensitize tumors to PLX4032.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. The terms in the claims have their plain, ordinary meaning unless otherwise explicitly and clearly defined by the patentee.

The following references may be cited herein:
1. Davies et al. Nature 2002; 417: 949-954.
2. Lito et al. Cancer Cell 2012; 22: 668-682.
3. Spagnolo et al. Oncotarget 2014; 5: 10206-10221.
4. Hauschild et al. Lancet 2012; 380: 358-365.
5. McArthur et al. Lancet Oncol 2014; 15: 323-332.
6. Johnson R, Halder G. Nat Rev Drug Discov 2014; 13: 63-79.
7. Harvey et al., Nat Rev Cancer 2013; 13: 246-257.
8. Lamar et al., Proc Natl Acad Sci USA 2012; 109: E2441-E2450.
9. Yuan et al., Int J Cancer 2015; 137: 638-645.
10. Menzel et al. Pigment Cell Melanoma Res 2014; 27: 671-673.
11. Nallet-Staub et al., J Invest Dermatol 2014; 134: 123-132.
12. Lin et al. Nat Genet 2015; 47: 250-256.
13. Kim et al., EMBO J 2016; 35: 462-478.
14. Zanconato F, Piccolo S. EMBO J 2016; 35: 459-461.
15. Michels S, Schmidt-Erfurth U. Semin Ophthalmol 2001; 16: 201-206.
16. Liu-Chittenden et al., Genes Dev 2012; 26: 1300-1305.
17. Donohue et al., J Cancer 2013; 4: 585-596.
18. Slemmons et al., PLoS One 2015; 10: e0140781.
19. Wagle et al., J Clin Oncol 2011; 29: 3085-3096.
20. Song et al. Clin Cancer Res 2015; 21: 2580-2590.
21. Errico A. Nat Rev Clin Oncol 2015; 12: 190.
22. Greten F R. Cell 2014; 158: 11-12.
23. Jerhammar et al., Oral Oncol 2014; 50: 832-839.
24. Lee et al., Clin Cancer Res 2015; 21: 357-364.
25. Liao et al., Oncotarget 2017; 8: 11719-11728.
26. Fisher et al., Mol Carcinog 2015; 55: 2024-2036.
27. Fisher et al., Cancer Res 2016; 76: 7265-7276.
28. Halder G, Johnson R L. Development 2011; 138: 9-22.
29. Huang et al., J Biol Chem 2012; 287: 26245-26253.
30. Gulshan et al., J Biol Chem 2012; 287: 26796-26805.
31. Wong et al., Mol Cancer 2014; 13: 194.
32. Joseph et al., Proc Natl Acad Sci USA 2010; 107: 14903-14908.
33. Lin et al., Mol Cell Oncol 2016; 3: e1021441.
34. Moroishi et al., Nat Rev Cancer 2015; 15: 73-79.
35. Santucci et al., J Med Chem 2015; 58: 4857-4873.
36. Zhang et al., Biochemistry 2015.
37. Zhao et al., Curr Opin Cell Biol 2008; 20: 638-646.
38. Adhikary et al., Carcinogenesis 2015; 36: 800-810.
39. Nakatani et al., The Journal of Biochemistry 2017; 161, 237-244.
40. Morris V et al., F1000Prime Rep. 2013; 5, 1-6.

What is claimed is:

1. A method of treating an individual having a BRAF inhibitor resistant melanoma consisting of:
administering to the individual having the BRAF inhibitor resistant melanoma a pharmacologically effective dose of Verteporfin and a pharmacologically effective dose of a BRAF inhibitor.

2. The method of claim 1, wherein the Verteporfin is administered at a pharmacologically effective dose of about 1 mg/kg to about 10 mg/kg.

3. The method of claim 1, wherein the BRAF inhibitor is vemurafenib, dabrafenib, encorafenib, methyl N-[6-[2-(5-chloro-2-methylphenyl)-1-hydroxy-3-oxoisoindol-1-yl]-1H-benzimidazol-2-yl] carbamate (BMS-098662), PLX3603, PLX4720 RAF265, and Sorafenib Tosylate.

4. The method of claim 3, wherein the BRAF inhibitor is vemurafenib, dabrafenib or encorafenib.

5. The method of claim 1, wherein the BRAF inhibitor is administered at a dosage of about 2 mg/kg to about 20 mg/kg.

6. The method of claim 1, wherein the BRAF inhibitor is administered before Verteporfin, after Verteporfin or with Verteporfin.

7. The method of claim 1, wherein the BRAF inhibitor resistant cancer has a BRAFV600 mutation, a BRAFR461 mutation, a BRAFI462 mutation, a BRAFG463 mutation, a BRAFG463 mutation, a BRAFG465 mutation, a BRAFG465 mutation, a BRAFG468 mutation, a BRAFN580 mutation, a BRAFE585 mutation, a BRAFD593 mutation, a BRAFF594 mutation, a BRAFG595 mutation, a BRAFL596 mutation, a BRAFT598 mutation, a BRAFV599 mutation, or a BRAFA727 mutation or a combination thereof.

8. The method of claim 7, wherein the BRAF inhibitor resistant cancer has a BRAFV600E mutation, a BRAFV600K mutation, a BRAFV600D mutation or a BRAFV600R mutation.

* * * * *